United States Patent [19]
Weston et al.

[11] Patent Number: 6,075,014
[45] Date of Patent: Jun. 13, 2000

[54] INHIBITORS OF β-LACTAMASES AND USES THEREFOR

[75] Inventors: Scott Weston, Wheaton; Brian Shoichet, Chicago, both of Ill.

[73] Assignee: Northwestern University, Evanston, Ill.

[21] Appl. No.: 09/096,893

[22] Filed: Jun. 12, 1998

Related U.S. Application Data

[60] Provisional application No. 60/049,992, Jun. 13, 1997.

[51] Int. Cl.[7] .................... A61K 31/69; A61K 31/445; A61K 31/44; A61K 31/35; A61K 31/27
[52] U.S. Cl. ..................... 514/64; 514/330; 514/340; 514/451; 514/456; 514/481; 514/543
[58] Field of Search ............... 514/64, 330, 340, 514/451, 456, 481, 543

[56] References Cited

U.S. PATENT DOCUMENTS

| | | | |
|---|---|---|---|
| 4,537,773 | 8/1985 | Shenvi | 514/63 |
| 5,574,017 | 11/1996 | Gutheil | 514/19 |
| 5,880,188 | 3/1999 | Austin et al. | 524/109 |

OTHER PUBLICATIONS

Windholz et al., *The Merck Index*, Ab No. 600 p. 83 & Ab No. 1913, p. 271 (1983).
Crompton et al., *Biochem. J.*, 251:453–459 (1988).
Martin et al., *Biorganic & Medicinal Chemistry Letters*, 4(10):1229–1234 (1994).
Thornsberry, *Pharmacotherapy*, 15(1Pt2):3S–8S (1995).
Weston et al., *J. Med. Chem.*, 41:4577–4586 (1998).
Amicosante et al., *J. Chemotherapy*, 1(6):394–398 (1989).
Beesley et al., *Biochem. J.*, 209:229–223 (1983).
Beesley et al., *Chem. Abstracts*, 9(17):135992q (1983).
Bennet et al., *Antimicrob. Agents Chemotherapy*, 37:153–158 (1993).
Davies, *Science*, 264:375–382 (1994).
Dryjanski et al., *Biochemisry*, 34(11):3561–3568 (1995).
Galleni et al., *Biochem. J.*, 250:753–760 (1988).
Kiener et al., *Biochem. J.*, 169:197–204 (1978).
Li et al., *Antimicrob. Agents Chemother.*, 39:1948–1953 (1995).
Lobkovsky et al., *Biochemistry*, 33:6762–6772 (1994).
Martin et al., *Chem. Abstracts*, 122(19):234072q (1995).
Neu, *Science*, 257:1064–1073 (1992).
Phillippon et al., *Antimicrob. Agents Chemother.*, 33:1131–1136 (1989).
Rolinson, *Rev. Infect. Diseases*, 13:S727–732 (1991).
Sanders, *Clinical Infectious Disease*, 14:1089–1099 (1992).
Saves et al., *J. Biol. Chem.*, 270:18240–18245 (1995).
Strynadka et al., *Nature*, 359:700–705 (1992).
Strynadka et al., *Nat. Struct. Biol.*, 3(3):233–239 (1996).
Strynadka et al., *Nat. Struct. Biol.*, 3(8):688–695 (1996).
Tomasz, *Rev. Infect. Dis.*, 8:S260–S278 (1986).
Usher et al., *Biochem.*, 37:16082–94 (1998).
Van Wersh, *Chem. Abstracts*, 87(3):23334x (1977).

*Primary Examiner*—Kevin E. Weddington
*Attorney, Agent, or Firm*—Sheridan Ross P.C.

[57] ABSTRACT

The invention provides novel non-β-lactam inhibitors of β-lactamases. In particular, the invention provides such inhibitors which are boronic acids of formula (1) which is set forth in the specification. These compounds may be used with β-lactam antibiotics to treat β-lactam-antibiotic-resistant bacterial infections. These compounds are also antibacterial by themselves. Finally, the invention provides a pharmaceutical composition comprising these compounds.

24 Claims, 12 Drawing Sheets

| POSITION | R | CODE |
|---|---|---|
| – | NONE | 2FDB |
| 2 | –CHO | 2FORMB |
| 3 | –NH$_2$ | MAPB |
| 4 | –CHO | 4FORMB |
| 4 | –CH$_3$ | 4MEPB |

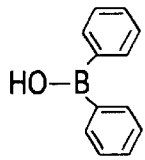
diphenylborinic acid
(DFB)

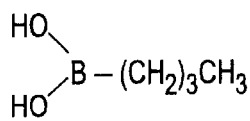
n-butylboronic acid
(BUTB)

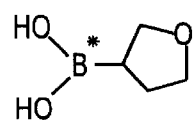
diethanolamine-
tetrahydrofuranylboronate
(RDETHFB & SDETHFB)

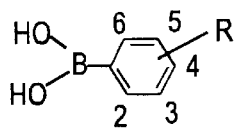

| POSITION | R | CODE | POSITION | R | CODE |
|---|---|---|---|---|---|
| — | NONE | 2FDB* | 4 | B(OH)$_2$ | B14DA |
| 2 | -CHO | 2FORMB* | 4 | -OCH$_3$ | 4MEOB |
|   |   |   | 4 | -CHO | 4FORMB |
| 3 | -CF$_3$ | 3TFMB | 4 | -CF$_3$ | 4TFMB |
|   |   |   | 4 | -Br | 4BPB |
| 3 | -NHSO$_2$-naphthyl-N(Me)$_2$ | NSULFB* | 4 | -C$_6$H$_4$-B(OH)$_2$ | BIPD |
| 3 | -NO$_2$ | 3NPB* | 2,5 | 2: -OH  5: -N=N-C$_6$H$_4$-CF$_3$ | HFAB |
| 3 | -NH$_2$ | MAPB* |   |   |   |
| 4 | -CH$_3$ | 4MEPB* | 2,5 | 2: -OH  5: -N=N-C$_6$H$_4$-Br | 4BPAPB |
| 4 | -CO$_2$H | 4COOHB |   |   |   |
| 4 | -F | 4FB |   |   |   |

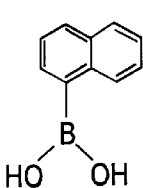
1-napthalene-
boronic acid
(NAPB)

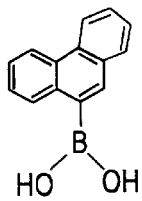
9-phenanthrene-
boronic acid
(9PHNB)

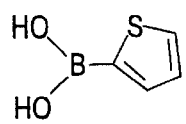
thiophene-2-
boronic
acid (TH2B)

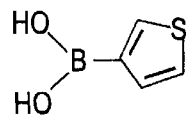
thiophene-3-
boronic
acid (TH3B)

FIG. 1D 3-formylthiophene-2-
boronic acid (3FTH2B)

5-chlorothiophene-2
boronic acid (5CLTH2B)

5-acetylthiophene-2
boronic acid (5ACTH2B)

benzo[b]thiophene-2
boronic acid (BZBTH2B)

benzo[b]furan-2 boronic
acid (BZBF2B)

INHIBITORS OF β-LACTAMASES AND USES THEREFOR

Benefit of provisional application No. 60/049,992, filed Jun. 13, 1997, is hereby claimed.

BACKGROUND

Bacterial resistance to antibiotics has raised fears of an approaching medical catastrophe (Neu, *Science*, 257, 1064–1073 (1992)). Evolutionary selection and genetic transformation have made this problem pressing. Most antibiotic drugs are derivatives of naturally occurring bactericides (Davies, *Science*, 264, 375–382 (1994)), and many resistance mechanisms evolved long ago. Human use of antibiotics has refined these mechanisms and promoted their spread through gene transfer (Davies, *Science,* 264, 375–382 (1994)). A resistance mechanism originating in one species of bacteria can be expected to spread throughout the biosphere.

Bacterial adaptations to β-lactam drugs (e.g., amoxicillin, cephalothin, clavulanate, aztreonam) are among the best studied and most pernicious forms of antibiotic resistance. β-lactams target enzymes that are unique to bacteria and are thus highly selective. They have been widely prescribed. In the absence of resistance, β-lactams are the first choice for treatment in 45 of 78 common bacterial infections (*Goodman & Gilman's The Pharmacological Basis of Therapeutics* (Hardman et al., eds., McGraw-Hill, New York, 1996)). The evolution of resistance to these drugs has raised the cost of antibiotic therapy and reduced its effectiveness, leading to increased rates of morbidity and mortality.

β-lactam antibiotics inhibit bacterial cell wall biosynthesis (Tomasz, *Rev. Infect. Dis.*, 8, S270–S278 (1986)). The drugs form covalent complexes with a group of transpeptidases/carboxypeptidases called penicillin binding proteins (PBPs). PBP inactivation disrupts cell wall biosynthesis, leading to self-lysis and death of the bacteria.

Bacteria use several different mechanisms to escape from β-lactam drugs (Sanders, *Clinical Infectious Disease*, 14, 1089–1099 (1992); Li et al., *Antimicrob. Agents Chemother.*, 39, 1948–1953 (1995)). Probably the most widespread is the hydrolysis of β-lactams by β-lactamase enzymes.

TEM-1 and AmpC are two β-lactamases from *Escherichia coli*. *E. coli* is an important pathogen in its own right. It is the most common cause of gram-negative bacterial infection in humans (Levine, *New Engl. J. Med.*, 313, 445–447 (1985)), and is the most prevalent hospital-acquired infection (Thornsberry, *Pharmacotherapy*, 15, S3-8 (1995)). *E. coli* that carry TEM-1, or for which AmpC production has been derepressed, are resistant to β-lactam treatment. As of 1992, as many of 30% of community-isolated *E. coli* and 40–50% of hospital-acquired *E. coli* in the United States were resistant to β-lactams such as amoxicillin (Neu, *Science*, 257, 1064–1073 (1992)). Many of these resistant *E. coli* are resistant to β-lactamase inhibitors such as clavulanic acid and sulbactam.

TEM-1 and AmpC are major forms of plasmid-based and chromosomal β-lactamases and are responsible for resistance in a broad host range. The versions of TEM and AmpC (Galleni, et al., *Biochem. J.*, 250, 753–760 (1988)) in other bacterial species share high sequence identity to TEM-1 and AmpC from *E. coli*. TEM-1 structurally and catalytically resembles the class A β-lactamase from *Staphlococcus aureus*. The structures of AmpC from *Citrobacter freundii* and *Enterobacter cloacae* have been determined, and they closely resemble the structure of the *E. coli* enzyme (K. Usher, L. Blaszczak, B. K. Shoichet, J. R. Remington, in preparation (1996)).

To overcome the action of β-lactamases, medicinal chemists have introduced compounds that inhibit these enzymes, such as clavulanic acid, or compounds that are less susceptible to enzyme hydrolysis, such as aztreonam. Both have been widely used in antibiotic therapy (Rolinson, *Rev. Infect. Diseases* 13, S727–732 (1991)); both are β-lactams. Their similarity to the drugs that they are meant to protect or replace has allowed bacteria to evolve further, maintaining their resistance.

Resistance to these new classes of β-lactams has arisen through modifications of previously successful mechanisms. Point substitutions in β-lactamases allow the enzymes to hydrolyze compounds designed to evade them (Philippon et al., *Antimicrob. Agents Chemother.*, 33, 1131–1136 (1989)). Other substitutions reduce the affinity of β-lactam inhibitors for the enzymes (Saves, et al., *J. Biol. Chem.*, 270, 18240–18245 (1995)) or allow the enzymes to simply hydrolyze them. Several gram positive bacteria, such as *Staph. aureus*, have acquired sensor proteins that detect β-lactams in the environment of the cell (Bennet and Chopra, *Antimicrob. Agents Chemotherapy*, 37, 153–158 (1993)). β-lactam binding to these sensors leads to transcriptional up-regulation of the β-lactamase. β-lactam inhibitors of β-lactamases, thus, can induce the production of the enzyme that they are meant to inhibit, defeating themselves.

It is noteworthy that the human therapeutic attack on bacteria has paralleled the path taken in nature. Several species of soil bacteria and fungi produce β-lactams, presumably as weapons against other bacteria (although this remains a matter of debate). Over evolutionary time, susceptible bacteria have responded to β-lactams with β-lactamases, among other defenses. In turn, soil bacteria have produced β-lactams that resist hydrolysis by β-lactamases or have produced β-lactams that inhibit the β-lactamases. *Streptomyces clavuligeris* makes several β-lactams, including clavulanic acid, a clinically used inhibitor of class A β-lactamases such as TEM-1. *Chromobacterium violaceum* makes aztreonam, a clinically used monobactam that resists hydrolysis by many β-lactamases. One reason why bacteria have been able to respond rapidly with "new" resistance mechanisms to β-lactams, and indeed many classes of antibiotics, is that the mechanisms are not in fact new. As long as medicinal chemistry focuses on new β-lactam molecules to overcome β-lactamases, resistance can be expected to follow shortly. The logic will hold for any family of antibiotic where the lead drug, and resistance mechanisms to it, originated in the biosphere long before their human therapeutic use. This includes the aminoglycosides, chloramphenicol, the tetracyclines and vancomycin.

One way to avoid recapitulating this ancient "arms race" would be to develop inhibitors that have novel chemistries, dissimilar to β-lactams. These non-β-lactam inhibitors would not themselves be degraded by β-lactamases, and mutations in the enzymes should not render them labile to hydrolysis. Novel inhibitors would escape detection by β-lactam sensor proteins that up-regulate β-lactamase transcription, and may be unaffected by porin mutations that limit the access of β-lactams to PBPs. Such inhibitors would allow current β-lactam drugs to work against bacteria where β-lactamases provide the dominant resistance mechansim.

It has previously been reported that boric acid and certain phenyl boronic acids are inhibitors of certain β-lactamases.

See, Kiener and Waley, *Biochem. J.*, 169, 197–204 (1978) (boric acid, phenylboronic acid (2FDB) and m-aminophenylboronate (MAPB)); Beesley et al., *Biochem. J.*, 209, 229–233 (1983) (twelve substituted phenylborinic acids, including 2-formylphenylboronate (2FORMB), 4-formylphenylboronate (4FORMB), and 4-methylphenylboronate (4MEPB)); Amicosante et al., *J. Chemotherapy*, 1, 394–398 (1989) (boric acid, 2FDB, MAPB and tetraphenylboronic acid). More recently, m-(dansylamidophenyl)-boronic acid (NSULFB) has been reported to be a submicromolar inhibitor of the *Enterobacter cloacae* P99 β-lactamase. Dryjanski and Pratt, *Biochemistry*, 34, 3561–3568 (1995). In addition, Strynadka and colleagues used the crystallographic structure of a mutant TEM-1 enzyme-penicillin G complex to design a novel alkylboronic acid inhibitor [(1R)-1-acetamido-2-(3-carboxyphenyl)ethane boronic acid] with high affinity for this enzyme. Strynadka et al., *Nat. Struc. Biol.*, 3, 688–695 (1996).

SUMMARY OF THE INVENTION

The invention provides non-β-lactam inhibitors of β-lactamases. In particular, the invention provides β-lactamase inhibitors having the formula:

(1)

$(OH)_2$—B—R wherein:

R is naphthalene, phenanthrene, or has one of the following formulas:

(2)

(3)
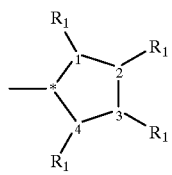

(4)
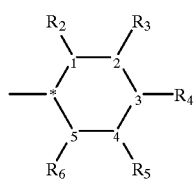

(5)
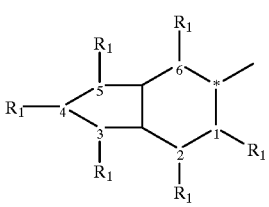

(6)
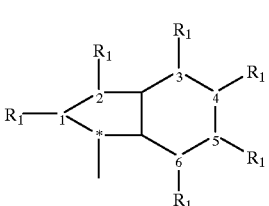

(7)
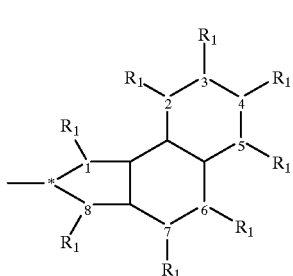

(8)
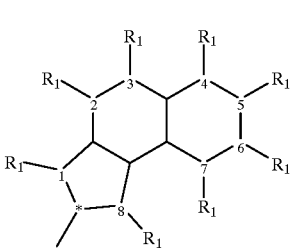

(9)
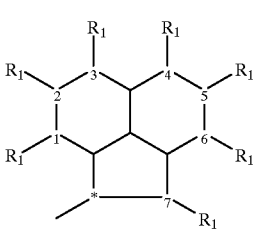

(10)
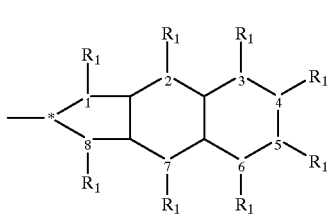

(11)
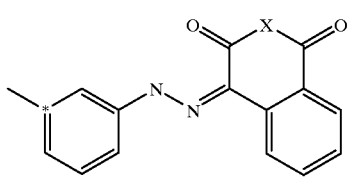

-continued

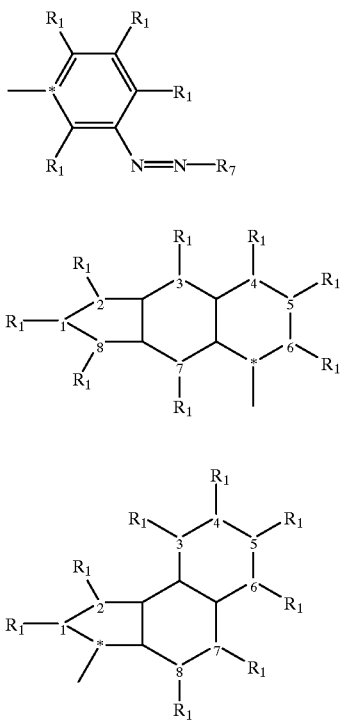

wherein:

ring system (2), (3), (4), (5), (6), (7), (8), (9) or (10) is aromatic or nonaromatic;

the atom center * is (R) or (S) in the case of chiral compounds;

positions 1, 2, 3, 4, 5, 6, 7 or 8 each independently is C, N, O or S;

$R_1$ through $R_6$ each independently is a lone pair, H, $B(OH)_2$, a halogen atom, $CF_3$, $CH_2CF_3$, $CCl_3$, $CH_2CCl_3$, $CBr_3$, $CH_2CBr_3$, $NO_2$, lower alkyl, $CO_2H$, CHCHCOOH, $CH_2CH_2CH_2COOH$, $SO_3H$, $PO_3H$, $OSO_3H$, $OPO_3H$, OH, $NH_2$, $CONH_2$, $COCH_3$, $OCH_3$, or phenyl boronic acid, except that $R_2$, $R_3$, $R_4$, $R_5$ and $R_6$ cannot all simultaneously be H, $R_2$ cannot be lower alkyl when $R_3$, $R_4$, $R_5$ and $R_6$ are H, $R_3$ cannot be $NH_2$, OH or lower alkyl when $R_2$, $R_4$, $R_5$ and $R_6$ are H, and $R_4$ cannot be lower alkyl when $R_2$, $R_3$, $R_5$ and $R_6$ are H;

$R_7$ is a lone pair, H, $B(OH)_2$, a halogen atom, $CF_3$, $CCl_3$, $CBr_3$, $CH_2CF_3$, $CH_2CCl_3$, $CH_2CBr_3$, $NO_2$, $CONH_2$, $COCH_3$, $OCH_3$, lower alkyl, aryl, aryl substituted with one or more substituents $R_8$, heteroaryl, or heteroaryl substituted with one or more substituents $R_8$;

each $R_8$ is independently a lone pair, H, $B(OH)_2$, a halogen atom, $CF_3$, $CCl_3$, $CBr_3$, $CH_2CF_3$, $CH_2CCl_3$, $CH_2CBr_3$, $NO_2$, lower alkyl, O, N, S, OH, $NH_2$, $N(CH_3)_2$, $N(CH_3)CH_2CH_3$, $NCOCH_3$, COOH, CHCHCOOH, $CH_2CH_2CH_2COOH$, $CONH_2$, $COCH_3$, $OCH_3$, OCl or phenyl boronic acid;

X is O, NH, $NCH_3$ or

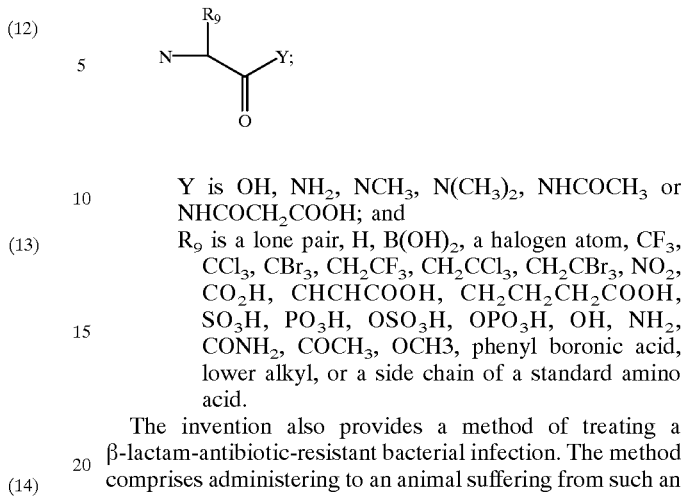

Y is OH, $NH_2$, $NCH_3$, $N(CH_3)_2$, $NHCOCH_3$ or $NHCOCH_2COOH$; and $R_9$ is a lone pair, H, $B(OH)_2$, a halogen atom, $CF_3$, $CCl_3$, $CBr_3$, $CH_2CF_3$, $CH_2CCl_3$, $CH_2CBr_3$, $NO_2$, $CO_2H$, CHCHCOOH, $CH_2CH_2CH_2COOH$, $SO_3H$, $PO_3H$, $OSO_3H$, $OPO_3H$, OH, $NH_2$, $CONH_2$, $COCH_3$, OCH3, phenyl boronic acid, lower alkyl, or a side chain of a standard amino acid.

The invention also provides a method of treating a β-lactam-antibiotic-resistant bacterial infection. The method comprises administering to an animal suffering from such an infection an effective amount of a β-lactamase inhibitor of formula (1), or a pharmaceutically-acceptable salt thereof, and an effective amount of a β-lactam antibiotic.

It has also been found that the compounds of formula (1), and pharmaceutically-acceptable salts thereof, are antibacterial by themselves. Thus, the invention further provides a method of treating a bacterial infection comprising administering to an animal suffering from such an infection an effective amount of a compound of formula (1), or a pharmaceutically-acceptable salt thereof.

Finally, the invention provides pharmaceutical compositions comprising compounds of formula (1), or pharmaceutically-acceptable salts thereof, and a pharmaceutically-acceptable carrier. The pharmaceutical compositions may also comprise β-lactam antibiotics.

BRIEF DESCRIPTION OF THE DRAWINGS

FIGS. 1A–E. Structures of boronic acids. FIG. 1A—boronic acids previously reported to be inhibitors of β-lactamase (prior art). FIGS. 1B and 1C—crystal structure of the complex of AmpC β-lactamase and the boronic acid inhibitor m-aminophenylboronic acid (MAPB). Note that the m-amino group of MAPB is not shown for clarity and that only the side-chains of most of the neighboring residues in the AmpC active site are shown for the same reason. The positions of the MAPB phenyl ring are numbered in both the 'top' (FIG. 1B) and 'back' (FIG. 1C) views. FIGS. 1D and 1E—boronic acid inhibitors of β-lactamases, including prior art inhibitors (marked with an *) and inhibitors according to the invention.

DETAILED DESCRIPTION OF THE PRESENTLY PREFERRED EMBODIMENTS OF THE INVENTION

Figure 1A:
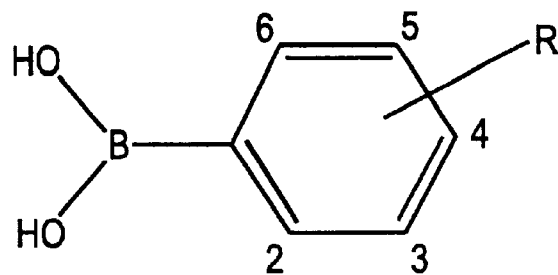
Figure 1A:
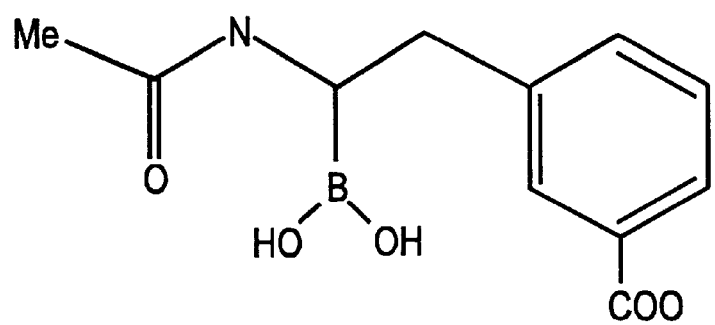
Figure 1B:
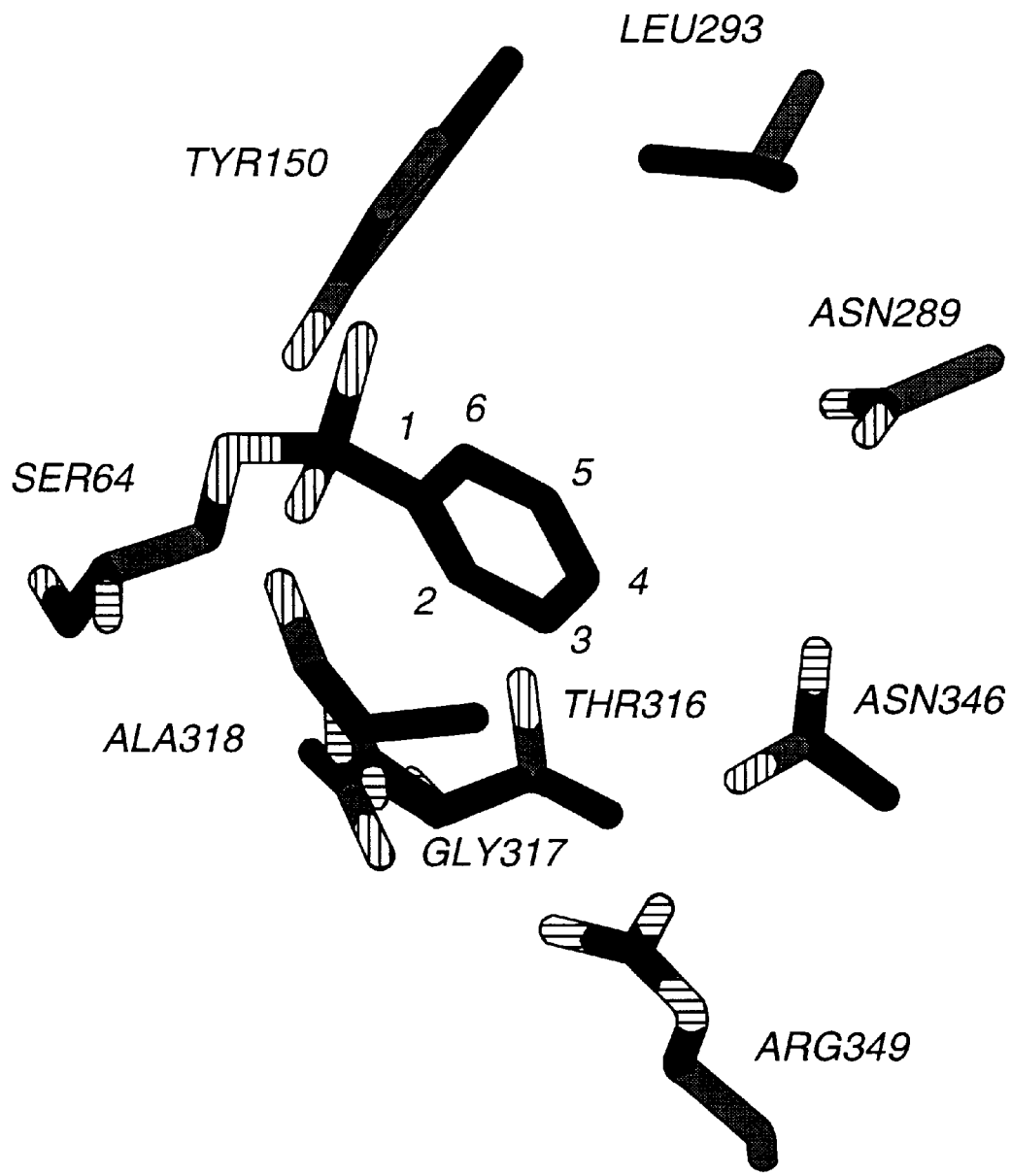
Figure 1C:
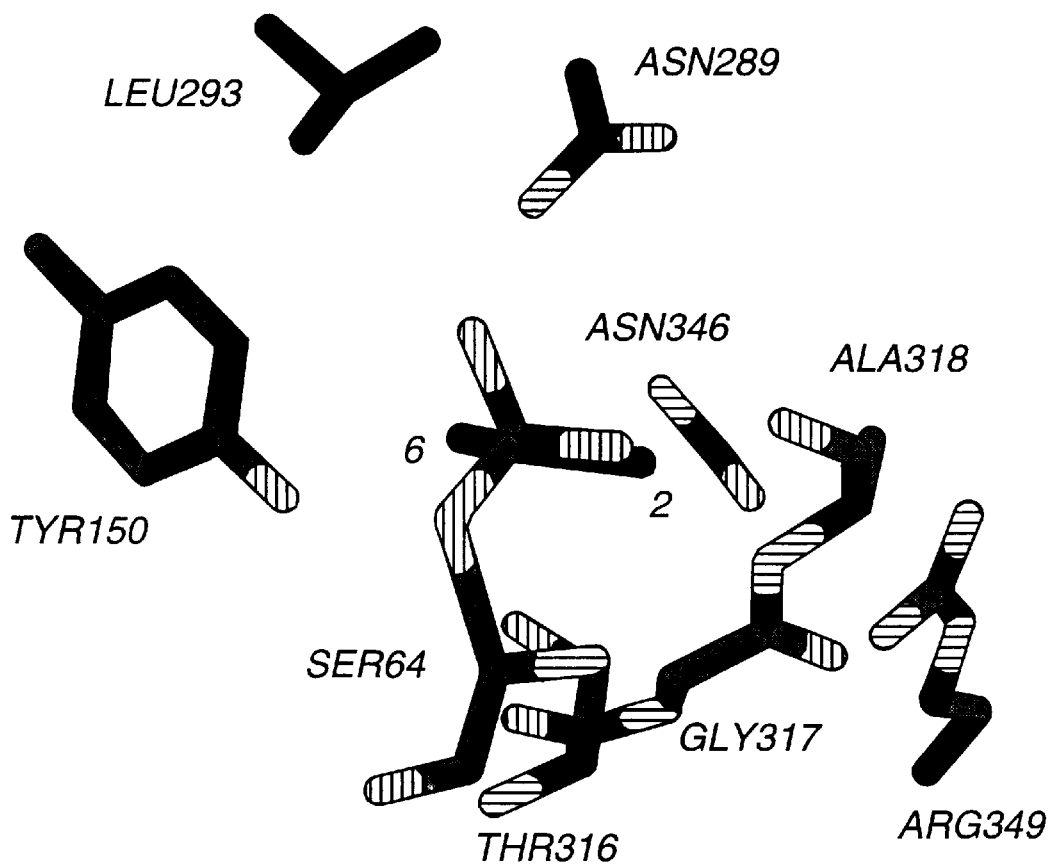

In formula (1) above, the following terms have the following meanings.

A "lone pair" refers to an unshared pair of electrons (not involved in an actual covalent chemical bond to another atom) that may have important interactions in receptor-ligand (e.g., enzyme-inhibitor) complexes.

"Alkyl" means a straight- or branched-chain alkyl containing 1–25 carbon atoms. "Lower alkyl" means a straight- or branched-chain alkyl containing 1–4 carbon atoms. Both of these terms include the R and S isomers.

"Aryl" means a structure containing from 1 to 3 aromatic rings, each ring containing from 5 to 6 carbon atoms.

"Heteroaryl" means an aryl as defined above wherein the ring(s) contain one or more atoms of S, N or O.

The "standard amino acids" are alanine, arginine, asparagine, aspartic acid, cysteine, glutamic acid, glutamine, glycine, histidine, homoserine, hydroxyproline, isoleucine, leucine, lysine, methionine, norleucine, norvaline, ornithine, penicillamine, phenylalanine, phenylglycine, proline, pyroglutamic acid, serine, threonine, tryptophan, tyrosine, and valine. Both the D and L isomers can be used. The side chains of these amino acids are well known and are the portions of the amino acids attached to the $NH_2$—CH—COOH backbone. For instance, the side chain of alanine is $CH_3$ and the side chain of asparagine is $CH_2CONH_2$.

The most preferred compounds of formula (1) are those wherein R is (4). Particularly preferred are those compounds wherein atom 1 of (4) is S or O, most preferably S, and the remaining atoms are carbons. Of this group of compounds, each $R_1$ is preferably H or each $R_1$ is H, except for the $R_1$'s attached to atoms numbers 3, 4 and 6. Preferably the $R_1$ attached to atom 6 is lower alkyl and the $R_1$'s attached to atoms 3 and 4 are small, polar and capable of forming hydrogen bonds. Most preferably the $R_1$ attached to atom 3 is COOH, CHCHCOOH or $CONH_2$, and the $R_1$ attached to atom 4 is $NH_2$. The most preferred compounds are benzo[b]furan-2-boronic acid and benzo[b]thiophene-2-boronic acid.

Other preferred compounds of formula (1) are those wherein R is (6). Particularly preferred are those compounds wherein atom 2 of (6) is S and the remaining atoms are carbons. Of this group of compounds, each $R_1$ is preferably H. The most preferred compound is benzo[b]thiophene-3-boronic acid.

Also preferred are compounds of formula (1) wherein R is (2). When R is (2), atom 1 is preferably S or atom 2 is preferably S or O. Most preferably atom 1 is S or atom 2 is O. Especially preferred compounds are thiophene-2-boronic acid, 3-formylthiophene-2-boronic acid, 5-chlorothiophene-2-boronic acid, 4-methylthiophene-2-boronic acid, 5-acetylthiophene-2-boronic acid, and R-3-tetrahydrofuranylboronic acid.

Other preferred compounds of formula (1) are those wherein R is (11). When R is (11), X preferably is O, $NCH_3$ or

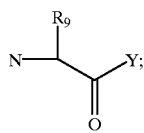

wherein Y is preferably $NH_2$ and $R_{19}$ is preferably the side chain of a polar, but not charged, amino acid (e.g., serine, threonine, asparagine and glutamine). Most preferred are 4-(3-boronatophenylazo)homophthalic anhydride and 4-(3-boronatophenylazo)-2-methylhomophthalimide.

Further preferred compounds of formula (1) include those wherein R is (3), and in (3) atoms 1–5 are all carbons and the ring is aryl. Preferred substituents $R_2$–$R_6$ include halogen, lower alkyl substituted with one or more halogen atoms (e.g., $CF_3$), $NO_2$, CHCHCOOH and phenyl boronic acid. More preferred are phenylboronic acid and $NO_2$, with $NO_2$ being the most preferred.

Additional preferred compounds of formula (1) include those wherein R is (12). Preferably $R_1$ is OH. Preferably $R_7$ is aryl or heteroaryl, unsubstituted or substituted with one or more substituents $R_8$. Most preferably $R_7$ is phenyl substituted with one or more substituents $R_8$. Most preferred are 2-hydroxy-5-(3-trifluoromethylphenylazo) benzeneboronic acid and 2,4,6-tris(5-(4-bromophenylazo)-2-hydroxyphenyl)boroxin.

The compounds of formula (1) are available commercially or can be synthesized as described below. Commercial sources of the compounds include TCI America, Portland, Oreg.; Key Organics, Cornwall, UK; Bionet, Cornwall, UK; Frontier Scientific, Logan, Utah; Aldrich Chemical, Milwaukee, Wis.; and Lancaster Synthesis, Windham, N.H.

Also, unless otherwise noted, the various chemicals used in the syntheses described below are available from commercial sources including Aldrich Chemical, Milwaukee, Wis., Lancaster Synthesis, Windham, N.H., TCI America, Portland, Oreg., Sigma Chemical Co., St. Louis, Mo., Acros Organics, Pittsburgh, Pa., Chemservice Inc., West Chester, Pa., BDH Inc., Toronto, Canada, Fluka Chemical Corp., Ronkonkoma, N.Y., Pfaltz & Bauer, Inc., Waterbury, Conn., Avocado Research, Lancashire, UK, Crescent Chemical Co., Hauppauge, N.Y., Fisher Scientific Co., Pittsburgh, Pa., Fisons Chemicals, Leicestershire, UK, ICN Biomedicals, Inc., Costa Mesa, Calif., Pierce Chemical Co., Rockford, Ill., Riedel de Haen AG, Hannover, Germany, Wako Chemicals USA, Inc., Richmond, Va., Maybridge Chemical Co. Ltd., Cornwall, UK, Trans World Chemicals, Inc., Rockville, Md., Apin Chemicals Ltd., Milton Park, UK, and Parish Chemical Co., Orem, Utah.

Figure 2A:
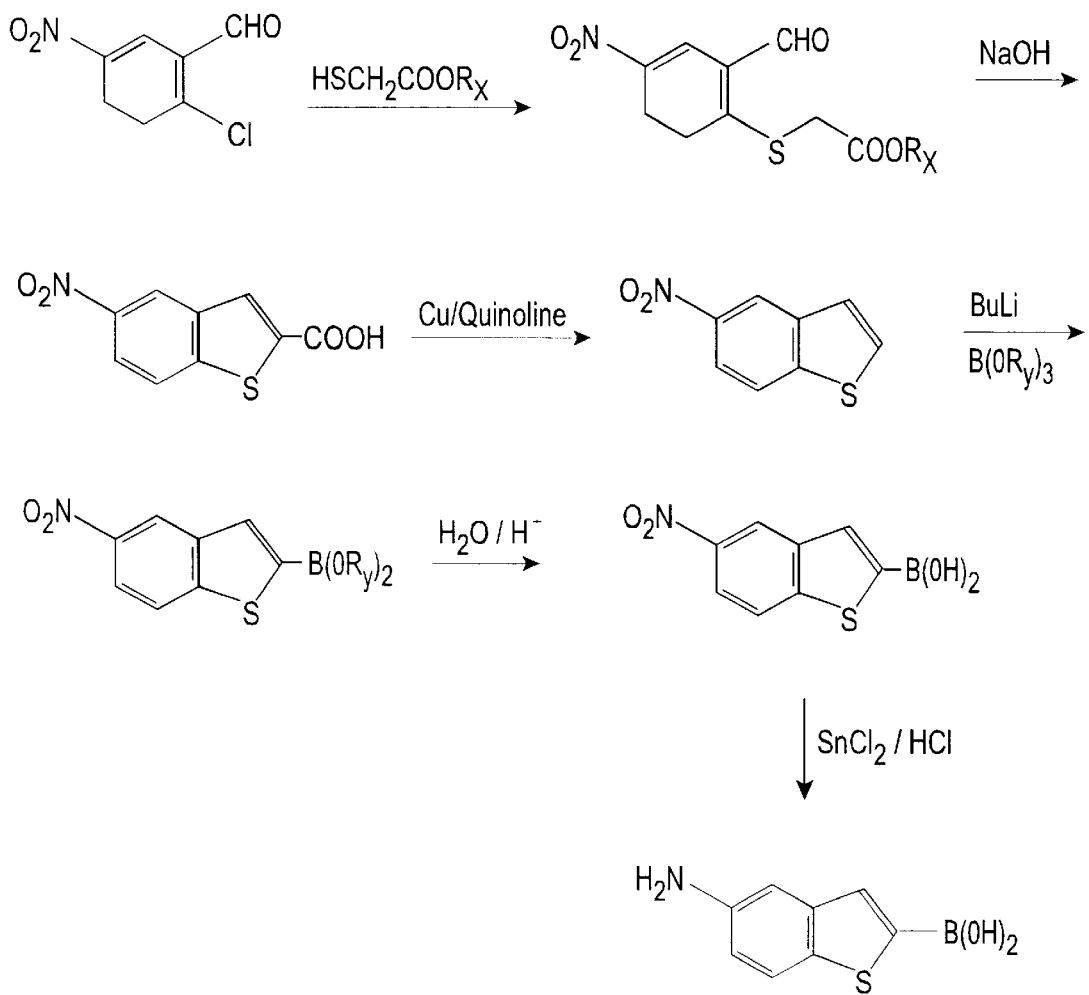
FIGS. 2A–C. Diagrams of the synthesis of compounds of formula (1) wherein R is (4).
Figure 2B:
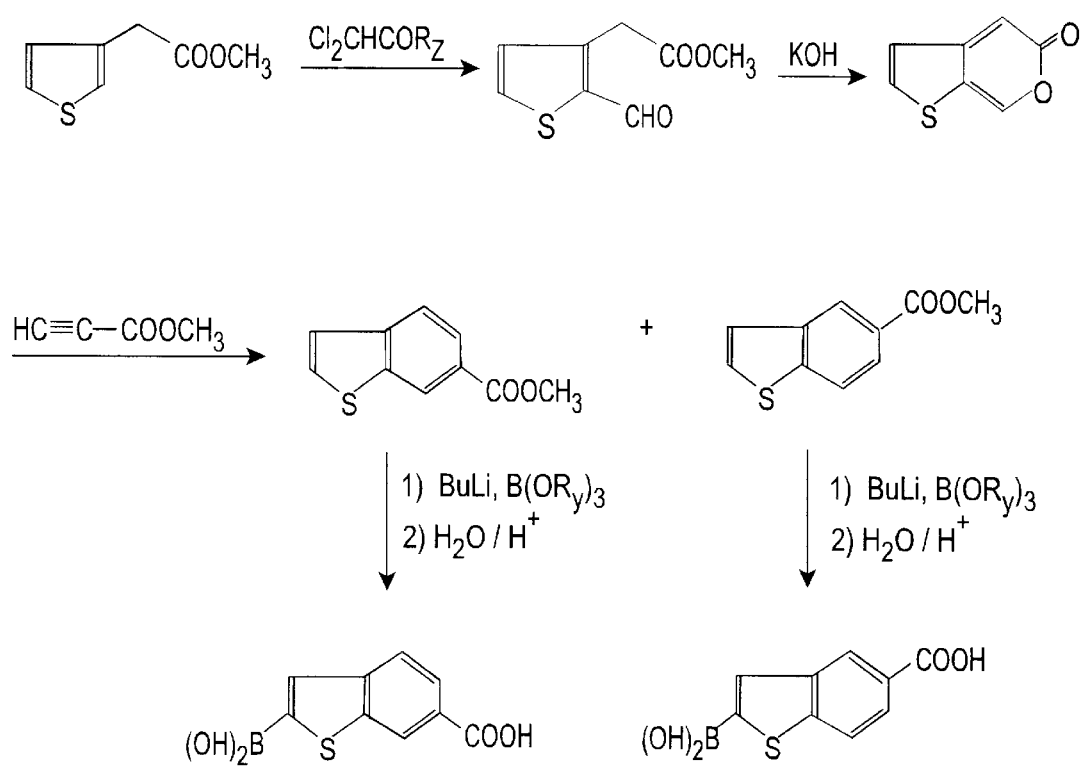
Figure 2C:
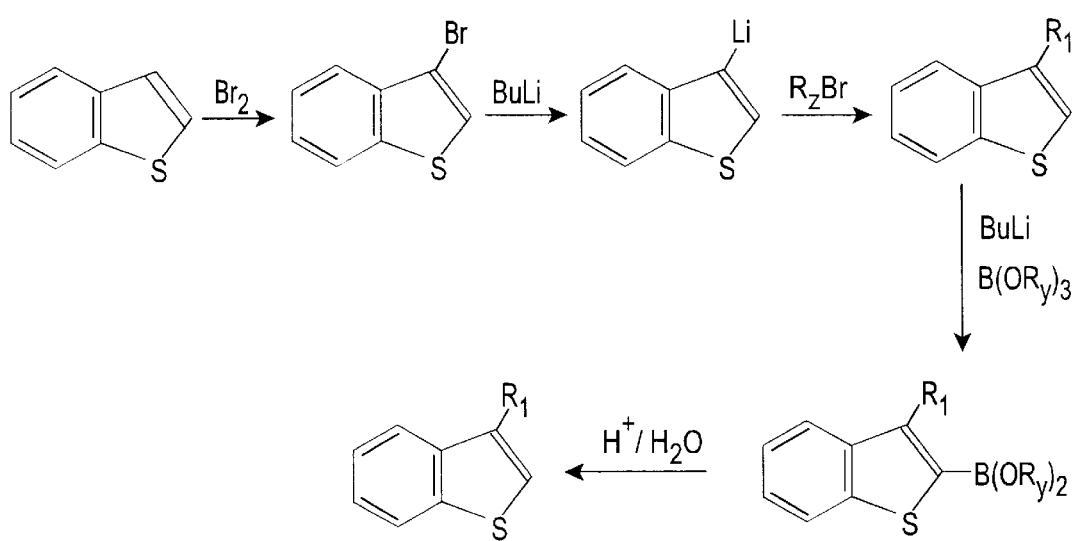

Compounds of formula (1) wherein R is (2)–(10), (13) and (14) can be synthesized as described in Beesley et al., *Biochem. J.*, 209, 229–233 (1983) or Matteson, *Acc. Chem. Res.*, 21, 294–300 (1988). Also see FIGS. 2A–C which diagram methods of synthesizing compounds of formula (1) wherein R is (4). In these figures, BuLi is butyl lithium. $R_x$, $R_y$ and $R_2$ may be any suitable leaving group such as lower alkyl, cycloalkyl, or phenyl. $R_1$ is defined above.

Figure 3:
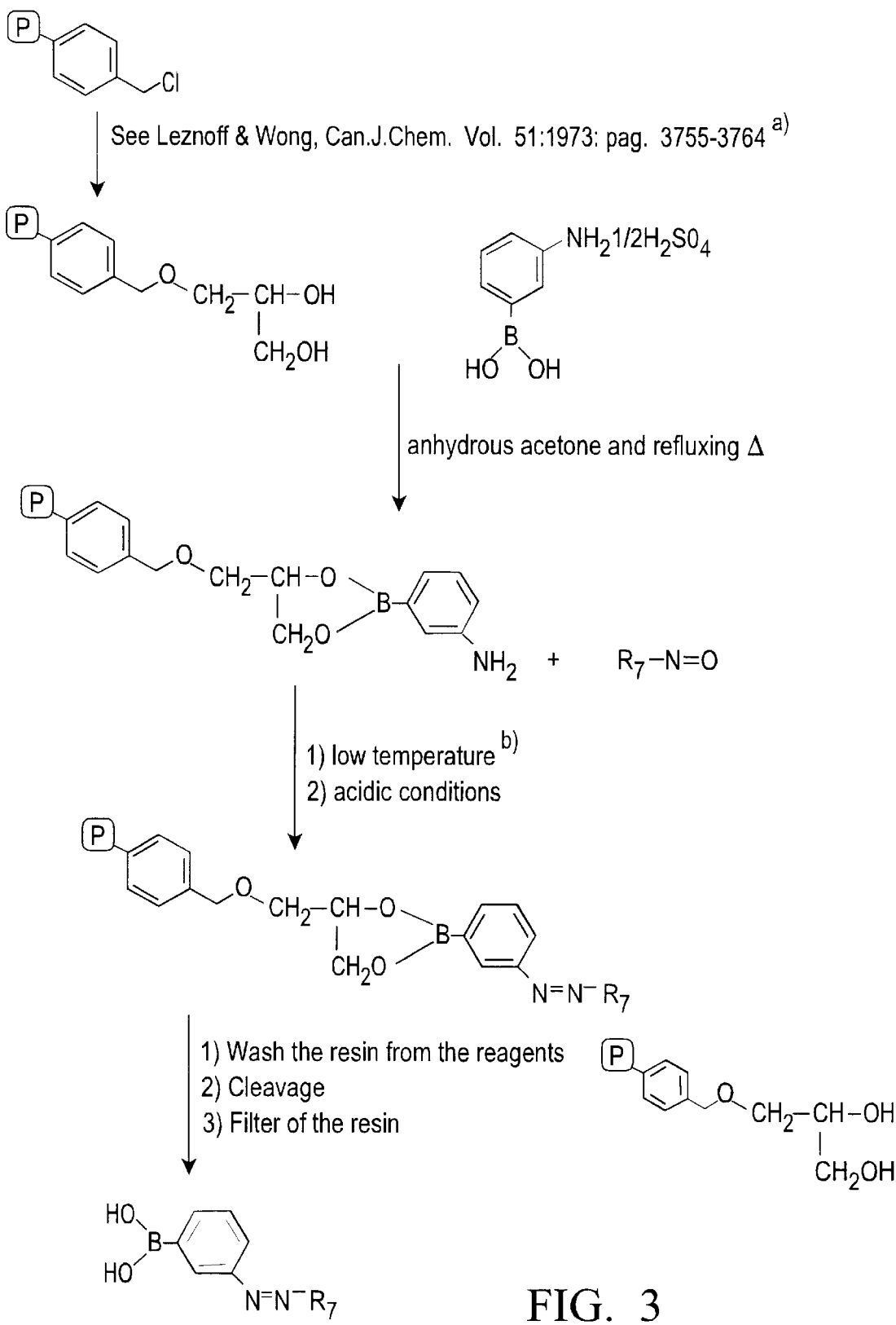
FIG. 3. Diagram of the synthesis of compounds of formula (1) wherein R is (12).

Compounds of formula (1) wherein R is (12) can be synthesized as depicted in FIG. 3 using $R_7$—N=O as the starting compound. The polystyrene resin, P, can be functionalized as described in Leznoff and Wong, *Can. J. Chem.*, 51:3756–3764 (1973). Alternatively, functionalized resins can be purchased from Novabiochem. The reaction (b) in FIG. 3 is called the Mills reaction. The selectivity of the hydrolysis in the Mills reaction is determined by the temperature, which should be kept low. Glacial acetic acid is used in this step when $R_7$ is aryl. However, the acidic conditions must be varied depending on the $R_7$ group, and other solvents and mineral acids are used. See March, *Advanced Organic Chemistry*, page 638 (4th ed. 1992) (John Wiley and Sons) and *The Chemistry Of Nitro and Nitroso Groups*, part 1, pages 278–283 (1969) (Interscience, New York). A modification of this reaction is described in Ayyangar et al., *Tetrahedron Letters*, 30, 7253 (1989) (starting with 3-N-acylphenyl boronic acid instead of 3-aminophenyl boronic acid).

Figure 4A:
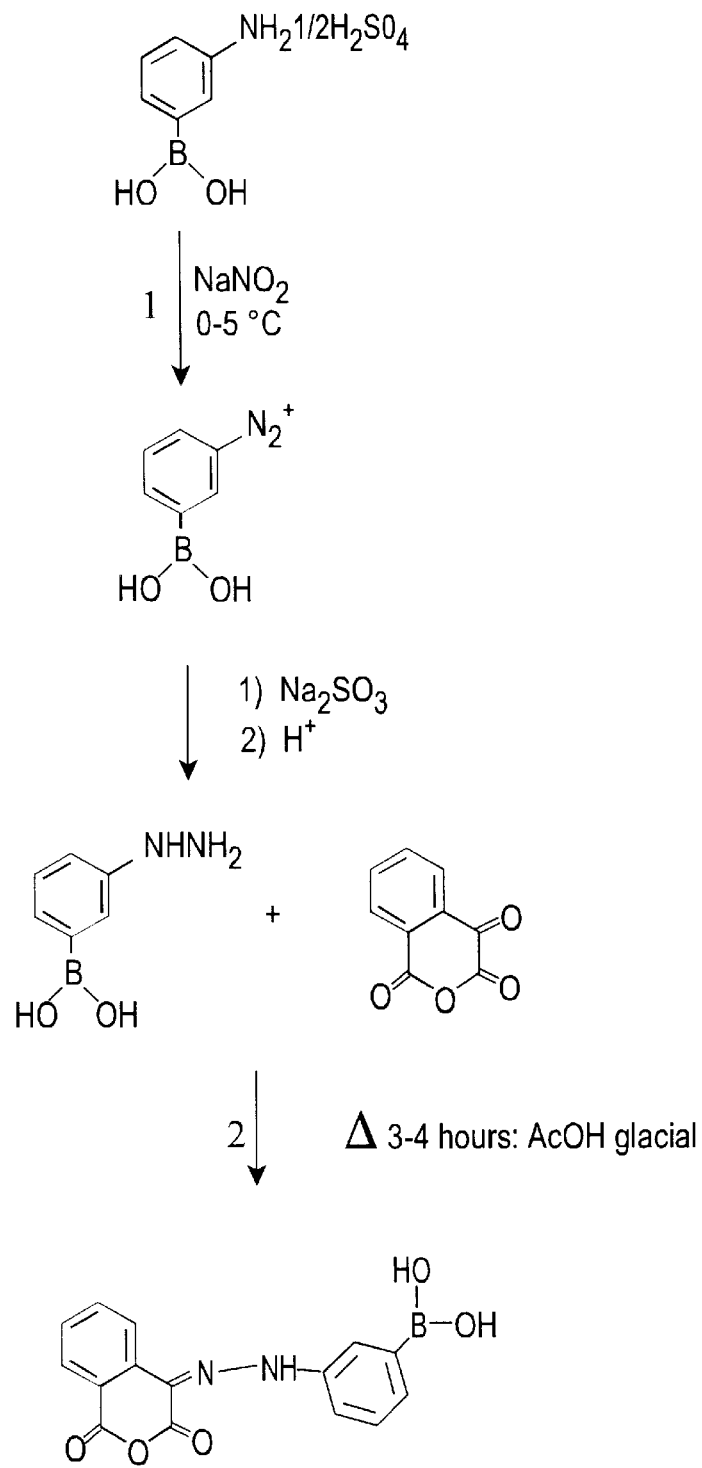
FIGS. 4A–B. Diagrams of the synthesis of compounds of formula (1) wherein R is (11).
Figure 4B:
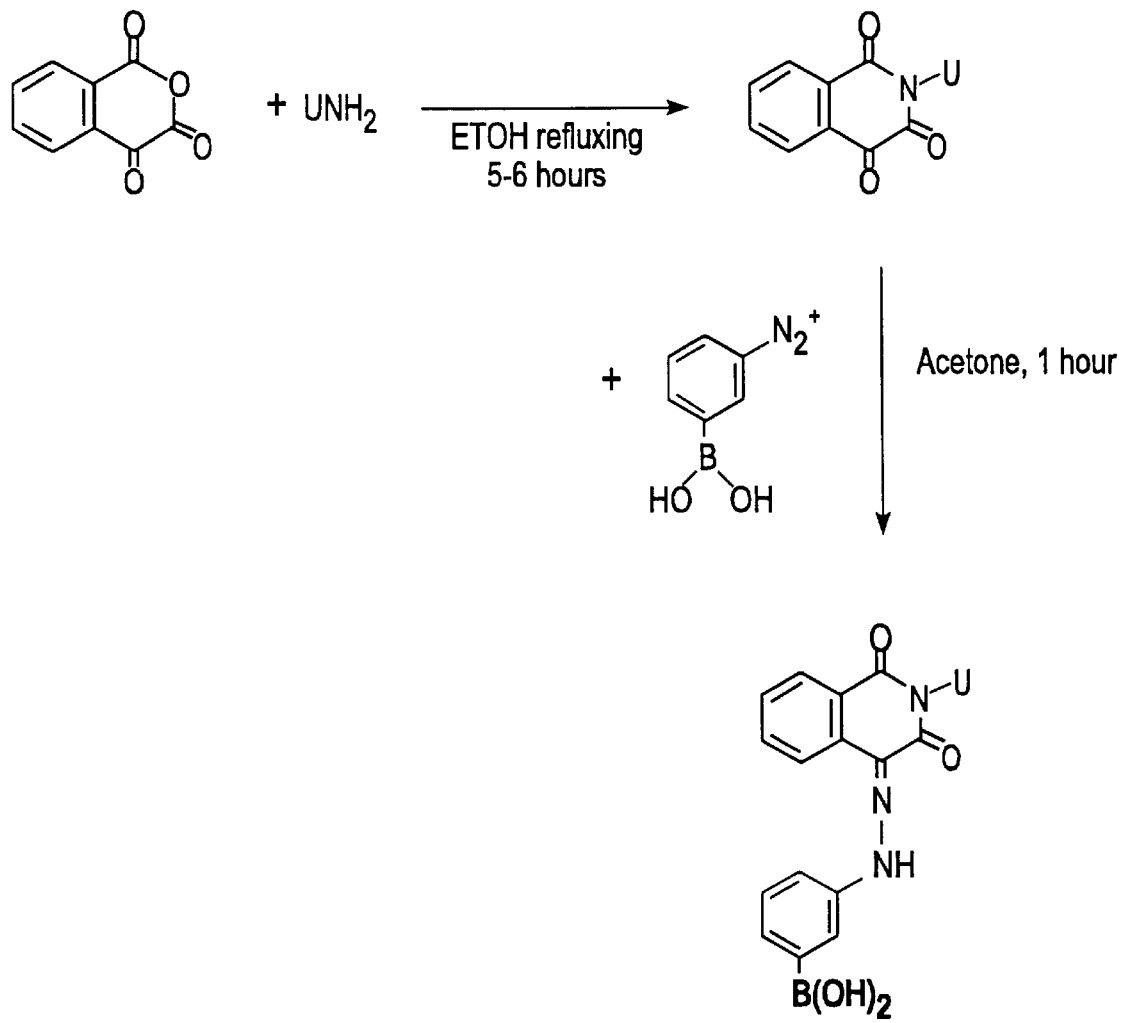

Finally, FIGS. 4A–B are diagrams of methods of synthesizing compounds of formula (1) wherein R is (11). In FIG.

4A, the reaction is preferably carried out using the free boronic acid as shown in FIG. 4A. However, functionalized resins can be used, as illustrated in FIG. 3. The use of such resins reduces the risk of secondary reactions due to steric hindrance. However, if the resin is used, the second step (reducing the diazonium salt to the hydrazine) will result in cleavage from the resin. In either case, the boronic acid can provide the acidic conditions for the reaction. In FIG. 4B, U is H, $CH_3$ or $R_0CH_2COY$. Compounds of formula (1) wherein R is (11) may also be obtained from Key Organics, Cornwall, U.K. (custom synthesis).

The compounds of formula (1) may contain an acidic or basic functional group and are, thus, capable of forming pharmaceutically-acceptable salts with pharmaceutically-acceptable acids and bases. The term "pharmaceutically-acceptable salts" in these instances refers to the relatively non-toxic, inorganic and organic acid and base addition salts of compounds of formula (1). These salts can be prepared by reacting the purified compound with a suitable acid or base. Suitable bases include the hydroxide, carbonate or bicarbonate of a pharmaceutically-acceptable metal cation, ammonia, or a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. Representative acid addition salts include the hydrobromide, hydrochloride, sulfate, phosphate, nitrate, acetate, valerate, oleate, palmitate, stearate, laurate, benzoate, lactate, phosphate, tosylate, citrate, maleate, fumarate, succinate, tartrate, napthalate, mesylate, glucoheptonate, lactobionate, and laurylsulphonate salts and the like.

The compounds of formula (1), and the pharmaceutically-acceptable salts thereof, are inhibitors of β-lactamases. As discussed in the Background, it has previously been reported that boric acid and certain boronic acids are inhibitors of certain β-lactamases. These inhibitors are different than the inhibitors of the invention defined by formula (1). Moreover, many of the compounds of formula (1) are much more effective inhibitors of β-lactamases than the prior art inhibitors (see the Examples below).

Assays for the inhibition of β-lactamase activity are well known in the art. For instance, the ability of a compound to inhibit β-lactamase activity in a standard enzyme inhibition assay may be used (see, e.g., Example 2 below and M. G. Page, *Biochem J.* 295 (Pt. 1) 295–304 (1993)). β-lactamases for use in such assays may be purified from bacterial sources or, preferably, are produced by recombinant DNA techniques, since genes and cDNA clones coding for many β-lactamases are known. See, e.g., S. J. Cartwright and S. G. Waley, *Biochem J.* 221, 505–512 (1984). Alternatively, the sensitivity of bacteria known, or engineered, to produce a β-lactamase to an inhibitor may be determined (see Example 3 below). Other bacterial inhibition assays include agar disk diffusion and agar dilution. See, e.g., W. H. Traub & B. Leonhard, *Chemotherapy* 43, 159–167 (1997). Inhibition includes both reduction and elimination of β-lactamase activity.

The compounds of formula (1) are also effective against bacteria resistant to β-lactam antibiotics as a result of porin mutations (see, e.g., Example 5 below). Porin mutations are mutations in the proteins which form porin channels in bacterial cell walls. These mutations reduce the ability of β-lactam antibiotics to enter bacterial cells in which the mutations occur, thereby making the bacteria resitant to these antibiotics.

The compounds of formula (1), or pharmaceutically-acceptable salts thereof, can be used to treat β-lactam-antibiotic-resistant bacterial infections. "β-lactam-antibiotic-resistant bacterial infection" is used herein to refer to an infection caused by bacteria resistant to treatment with β-lactam antibiotics due primarily to the action of a β-lactamase, a porin mutation, or both. Resistance to β-lactam antibiotics can be determined by standard antibiotic sensitivity testing. The presence of β-lactamase activity can be determined as is well known in the art (see above). The presence of a porin mutation can be detected by polymerase chain reaction analysis of porin genes, polyacrylamide gel electrophoresis of a preparation obtained by mild osmotic shock (e.g., treatment with hypotonic solution containing EDTA, followed by gentle centrifugation and separation of the supernatant) of the bacteria (absence of a protein of the appropriate molecular weight being indicative of a porin mutation), or by determining resistance to infection by bacteriophage Tu1A (a standard test for $OmpF^-$ porin mutations). Alternatively, and preferably, the sensitivity of a particular bacterium to the combination of a compound of formula (1), or a pharmaceutically-acceptable salt thereof, and a β-lactam antibiotic can be determined by standard antibiotic sensitivity testing methods.

To treat a β-lactam resistant bacterial infection, an animal suffering from such an infection is given an effective amount of a compound of formula (1), or a pharmaceutically-acceptable salt thereof, and an effective amount of a β-lactam antibiotic. The compound of formula (1), or a pharmaceutically-acceptable salt thereof, and the antibiotic may be given separately or together. When administered together, they may be contained in separate pharmaceutical compositions or may be in the same pharmaceutical composition.

Many suitable β-lactam antibiotics are known. These include cephalosporins (e.g., cephalothin), penicillins (e.g., amoxicillin), monobactams (e.g., aztreonam), carbapenems (e.g., imipenem), carbacephems (loracarbef), and others. β-lactam antibiotics are effective (in the absence of resistance) against a wide range of bacterial infections. These include those caused by both gram-positive and gram-negative bacteria, for example, bacteria of the genus Staphylococcus (such as *Staphylococcus aureus* and *Staphylococcus epidermis*), Streptococcus (such as *Streptococcus agalactine, Streptococcus penumoniae* and *Streptococcus faecalis*), Micrococcus (such as *Micrococcus luteus*), Bacillus (such as *Bacillus subtilis*), Listerella (such as *Listerella monocytogenes*), Escherichia (such as *Escherichia coli*), Klebsiella (such as *Klebsiella pneumoniae*), Proteus (such as *Proteus mirabilis* and *Proteus vulgaris*), Salmonella (such as *Salmonella typhosa*), Shigella (such as *Shigella sonnei*), Enterobacter (such as *Enterobacter aerogenes* and *Enterobacter facium*), Serratia (such as *Serratia marcescens*), Pseudomonas (such as *Pseudomonas aeruginosa*), Acinetobacter such as *Acinetobacter anitratus*), Nocardia (such as *Nocardia autotrophica*), and Mycobacterium (such as *Mycobacterium fortuitum*). Effective doses and modes of administration of β-lactam antibiotics are known in the art or may be determined empirically as described below for the compounds of formula (1).

It has also been found that the compounds of formula (1), or pharmaceutically-acceptable salts thereof, are antibacterial by themselves, although at higher concentrations than β-lactam antibiotics. Indeed, they have shown activity against β-lactam-antibiotic-resistant bacteria. Although not wishing to be bound by any particular theory, it is believed that this antibacterial activity is due to the binding of the inhibitors to PBPs which resemble β-lactamases. Since PBPs are found in all bacterial species susceptible to β-lactam antibiotics, it is expected that the compounds of formula (1), or pharmaceutically-acceptable salts thereof, will be effective against the same bacteria as the β-lactam antibiotics (see above). As with the β-lactam antibiotics, sensitivity of bacteria to the compounds of formula (1), or pharmaceutically-acceptable salts thereof, can be determined by standard antibiotic sensitivity testing.

To treat an animal suffering from a bacterial infection, including β-lactam-antibiotic-resistant bacterial infections, an effective amount of a compound of formula (1), or a pharmaceutically-acceptable salt thereof, is administered to the animal, alone or in combination with a β-lactam antibiotic. Effective dosage forms, modes of administration and dosage amounts of a compound of formula (1), may be determined empirically, and making such determinations is within the skill of the art. It is understood by those skilled in the art that the dosage amount will vary with the activity of the particular compound employed, the severity of the bacterial infection, whether the bacterial infection is resistant to treatment with β-lactam antibiotics, the route of administration, the rate of excretion of the compound, the duration of the treatment, the identity of any other drugs being administered to the animal, the age, size and species of the animal, and like factors well known in the medical and veterinary arts. In general, a suitable daily dose will be that amount which is the lowest dose effective to produce a therapeutic effect. The total daily dosage will be determined by an attending physician or veterinarian within the scope of sound medical judgment. If desired, the effective daily dose of a compound of formula (1), or a pharmaceutically-acceptable salt thereof, may be administered as two, three, four, five, six or more sub-doses, administered separately at appropriate intervals throughout the day. Treatment of a bacterial infection, including β-lactam-antibiotic-resistant bacterial infections, according to the invention, includes mitigation, as well as elimination, of the infection.

Animals treatable according to the invention include mammals. Mammals treatable according to the invention include dogs, cats, other domestic animals, and humans.

Compounds of formula (1) or pharmaceutically-acceptable salts thereof, may be administered to an animal patient for therapy by any suitable route of administration, including orally, nasally, rectally, intravaginally, parenterally, intracisternally and topically, as by powders, ointments or drops, including buccally and sublingually. The preferred routes of administration are orally and parenterally.

While it is possible for the active ingredient(s) (one or more compounds of formula (1), or pharmaceutically-acceptable salts thereof, alone or in combination with a β-lactam antibiotic) to be administered alone, it is preferable to administer the active ingredient(s) as a pharmaceutical formulation (composition). The pharmaceutical compositions of the invention comprise the active ingredient(s) in admixture with one or more pharmaceutically-acceptable carriers and, optionally, with one or more other compounds, drugs or other materials. Each carrier must be "acceptable" in the sense of being compatible with the other ingredients of the formulation and not injurious to the patient.

Pharmaceutical formulations of the present invention include those suitable for oral, nasal, topical (including buccal and sublingual), rectal, vaginal and/or parenteral administration. Regardless of the route of administration selected, the active ingredient(s) are formulated into pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s). The active ingredient(s) may also be administered as a bolus, electuary or paste.

In solid dosage forms of the invention for oral administration (capsules, tablets, pills, dragees, powders, granules and the like), the active ingredient(s) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredients) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredients) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Dosage forms for the topical or transdermal administration of the active ingredient(s) include powders, sprays, ointments, pastes, creams, lotions, gels, solutions, patches and inhalants. The active ingredient(s) may be mixed under sterile conditions with a pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

Pharmaceutical compositions of this invention suitable for parenteral administration comprise the active ingredient(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredients) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly (orthoesters) and poly(anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

EXAMPLES

Example 1
Identification of Potential β-Lactamase Inhibitors

To target sites on the *E. coli* TEM-1 and AmpC β-lactamases to which novel inhibitors might bind, the structures of certain enzyme-inhibitor complexes were determined. These structures and other known structures of enzyme-inhibitor and enzyme-substrate complexes were used to define the binding sites of the enzymes. Additional potential binding sites on AmpC were identified using computational methods.

TEM-1 and AmpC were chosen because, as discussed above, these two β-lactamases are responsible for resistance to β-lactam antibiotics in *E. coli*, and the versions of TEM and AmpC in other bacterial species share high sequence identity and are structurally similar to TEM-1 and AmpC from *E. coli*. The high degree of species similarity among the TEM and AmpC β-lactamases suggests that inhibitors discovered for the *E. coli* enzymes will be active against Types I and II 62 -lactamases in other bacterial species. This is consistent with the antimicrobial data presented below which show that the boronic acid derivatives of the invention are active against bacteria expressing several different type I and type II TEM-1 β-lactamases (e.g., the AmpC-like enzyme expressed by *Enterobacter cloacae*).

AmpC was expressed in *E. coli* JM109 cells in which the native AmpC gene was attenuated or completely removed (obtained from Larry Blaszczak, Eli Lilly and Co., Indianapolis, Ind.). DNA coding for the enzyme was located on a plasmid under the control of a temperature sensitive repressor. Cells containing this plasmid were grown in 2 liters of LB broth in a fermentor to log phase. Enzyme expression was then induced by temperature shock, and the cells were allowed to grow overnight. AmpC protein was purified from the supernatant over an Affigel-10 aminophenyl boronate affinity column (Bio-Rad Laboratories, 1000 Alfred Nobel Drive, Hercules, Calif.). The purity of the sample was estimated by HPLC to be 96% or better. The amount of enzyme produced was estimated to be 150 mg based on absorbance at 280 nm.

Protein from this preparation was used to grow diffraction-quality crystals. The structures of three boronate-enzyme complexes (m-aminophenylboronic acid (MABP), benzo[b]thiophene-2-boronic acid (BZBTH2B) and m-nitrophenylboronic acid (3NPB)) were also determined. Protein crystals were obtained by vapor diffusion using a hanging drop method. The concentration of protein in the drops was 3–6 mg/ml, and the concentration of the boronic acid inhibitor was 1–10 mM. The buffer in the well was 1.7 M potassium phosphate, pH 8.7. For the MAPB-AmpC complex, 2% methane pentane diol was also used. For the MAPB-AmpC complex, x-ray diffraction data were collected on a Xuong-Hamlin multiwire detector. For the BZBTH2B-AmpC and 3NPB-AmpC complexes, data were collected on an R-axis image plate system. The structure of the MAPB-AmpC complex was refined with the program TNT (D. E. Tronrud, *Acta Crystallogr. Sect.* A. 48 912–916 (1992)). The structures of the BZBTH2B-AmpC and 3NPB-AmpC complexes were refined with the program X-Plor (Brunger, A. T., *X-PLOR Version* 3.1 *A System For X-ray Crystallography And NMR* (Yale University Press, New Haven, Conn., 1992). For all three boronic acid-AmpC complex structures, models were built with the program 0 (Jones et al., *Acta Crystallogr. Sect* A 47, 110–119 (1991)). The x-ray crystallographic statistics for these three complexes are given in Table 1 below. The structures of the three boronate complexes and the structure of the phosphonate complex of Knox and colleagues (Lobkovsky, et al., *Biochemistry*, 33, 6762–6772 (1994)) were used to partly define the binding sites of AmpC.

For TEM-1 the structures of three inhibitor-enzyme complexes determined by Natalie Strynadka (Strynadka et al., *Nature*, 359, 700–705 (1992); Strynadka et al., *Nature Structural Biology*, 3, 233–239 (1996); Strynadka et al., *Nat. Struct. Biol.*, 3, 688–695 (1996)) were used to define the binding sites of TEM-1. These complexes were a protein-protein complex involving a β-lactamase inhibitory protein, a complex with penicillin G, and a complex with a boronate inhibitor.

Using the computational methods of Kuntz (Kuntz et al., *J. Mol. Biol.*, 161, 269–288 (1982)) and Honig (Gilson and Honig, *Nature*, 330, 84–86 (1987)), additional potential binding sites in a tunnel region of AmpC that the various inhibitors did not take advantage of, but which seemed to be present in the structure of the enzyme, were identified.

Using the binding sites defined as described above, other boronic acids were identified as potential inhibitors of β-lactamase. 2-Phenylboronic acid, MABP, thiophene-2-boronic acid (TH2B), 3NPB, and 4,4'-biphenyldiboronic acid (BIPD) were selected as a representative sample of commercially-available boronic acids for modeling into the AmpC active site. Structures and conformational libraries for each compound were created using the Sybyl molecular modeling suite (Tripos Inc., St. Louis, Mo.). Conformer interactions with AmpC were scored based on steric and electrostatic criteria using the DISTMAP (Shoichet, B. K.; Bodian, D. L.; Kuntz, I. D., *J. Comp. Chem.*, 13, 380–397 (1992)) and DelPhi (Gilson, M. K.; Honig, B. H., *Nature*, 330, 84–86 (1987)) programs (Table 1). Two major families of ligand orientations were identified. In one "MAPB-like" mode, the boronic acid ligand is oriented similarly to the inhibitor in the MAPB-AmpC structure and is predicted to interact with residues Thr316, Asn346, and Asn289. In a second "phosphonate-like" mode, the boronic acid ligand is oriented similarly to the phosphonate ligand in an AmpC-inhibitor complex determined by Lobkovsky, et al. (Lobkovsky, E.; Billings, E. M.; Moews, P. C.; Rahil, J.; Pratt, R. F.; Knox, J. R. *Biochemistry*, 33, 6762–6772 (1994)) and is predicted to interact with residues Asn152 and Gln120. The numbering scheme used to refer to *E. coli* AmpC residues is that of Galleni et al. Galleni et al., Sequence and Comparative Analysis of Three *Enterobacter cloacae* ampC β-Lactamase Genes and Their Products, *Biochem. J.* 250:753–760 (1988).

Several predictions arose out of these modeling studies. The distribution of orientations in the two modes was generally correlated with the size of the boronic acid ligand, with larger ligands favoring the "phosphonate-like" mode because of steric clashes with the receptor in the "MAPB-like" mode. Ligands such as TH2B, which might bind in an "MAPB-like" conformation, would be expected to have specific interactions with features of the AmpC binding site that might improve their potency relative to AmpC. Larger ligands, such as BZBTH2B, were expected to bind in the "phosphonate-like" geometry. In this latter geometry, ligands such as BZBTH2B and 3NPB would be expected to interact with Gln120, Asn152 and Tyr150.

Figure 5:
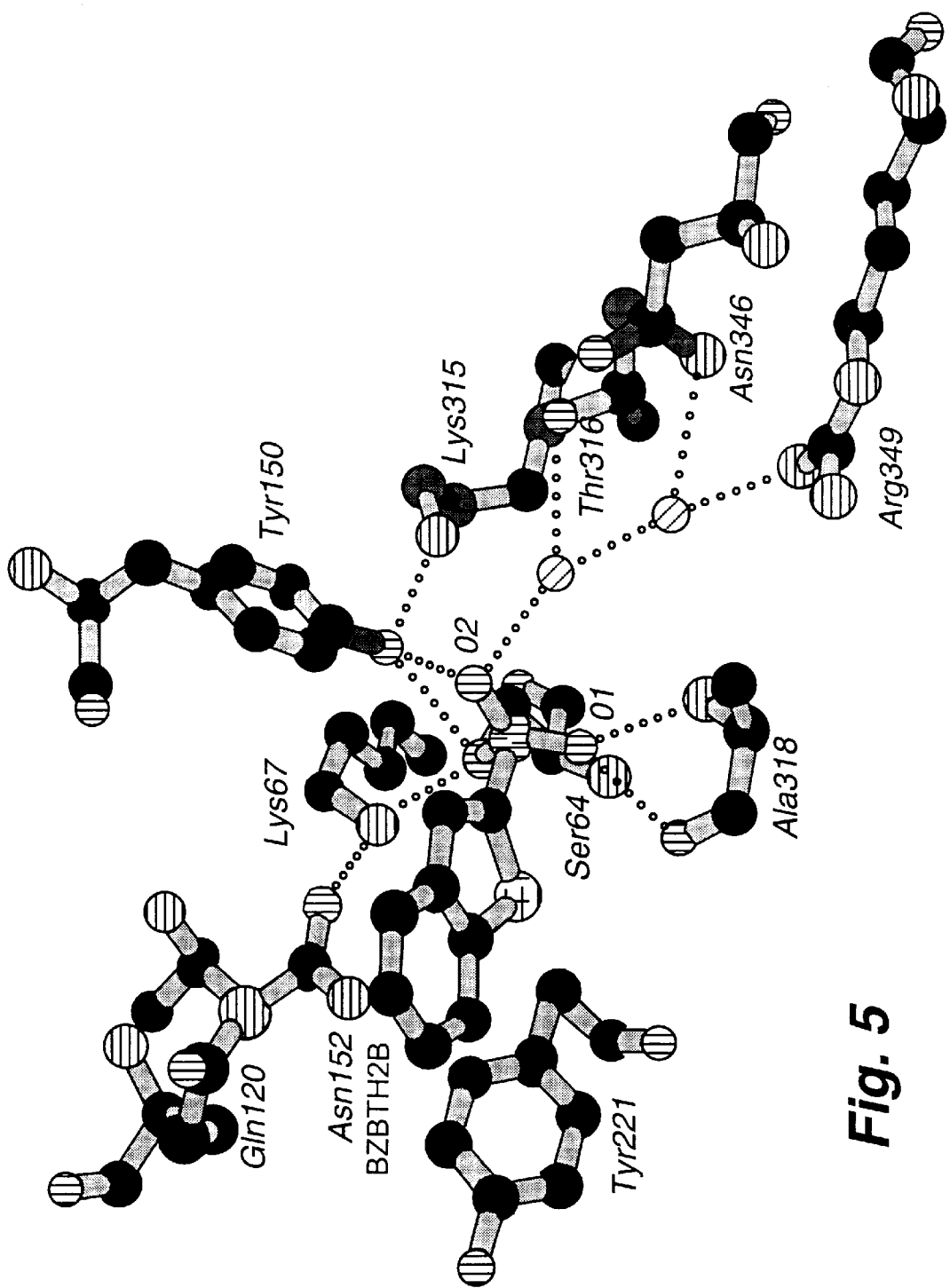
FIG. 5. Representation of the environment around β-lactamase inhibitor benzo[b]thiophene-2-boronic acid (BZBTH2B) showing key active site residues of the enzyme.

The geometries of BZBTH2B and 3NPB in complex with AmpC, determined by x-ray crystallography, are consistent with these predictions. A refined structure of BZBTH2B (2Fo-Fc electron density) showed the inhibitor covalently connected to serine 64 (Ser64). The density clearly defined the orientation of this compound in the binding site. The crystallographic statistics were good (R-factor 0.179, Rfree 0.229), and all bond and angle values fell within the allowed deviations for a well-refined structure. A similar refined structure of 3NPB (2Fo-Fc electron density) showed that this inhibitor was also covalently connected to Ser64. FIG. 5 shows key active site residues of the enzyme environment around BZBTH2B. Residues displayed were typically within 5 angstroms of BZBTH2B, with the exception of Arg349 and Asn346. These last two residues are nevertheless part of a polar network that interacts with the O2 hydroxyl of BZBTH2B through two well-defined water molecules (small spheres). The dotted lines indicate hydrogen bond interactions, with atoms within 2.6–3.2 angstroms of each other. The atomic resolution nature of these x-ray structures clearly showed the interactions that these inhibitors are making with AmpC and provide a strong framework for identifying and designing future boronic acid inhibitors of the enzyme.

by steric constraints. 2-naphthylboronic acid has an affinity ($K_i$=8.5±1.8 $\mu$M) comparable to MAPB, suggesting that the presence of a larger hydrophobic substituent in the right orientation does not hinder binding. Certainly for diphenylboronic acid, which lacks measurable inhibition of AmpC, modeling suggests potential steric conflicts with residues Tyr150 and Lys67. On the other hand, the smaller and more flexible n-butylboronic acid should have little difficulty fitting into the AmpC site, and yet it also displays no measurable inhibition of AmpC. Taken together, these results suggest that boronic acids must have the correct stereochemical arrangement of functionality; hydrophobicity alone is not sufficient to explain affinity.

The differential affinities of the boronic acids for AmpC might be due to activation of the boronic acid group as an electrophile by substituents on the aryl ring. The affinities of 2-formyl- and 4-formyl-phenylboronic acids, and those of 3-trifluoro- and 4-trifluoro-phenylboronic acids were compared. If affinity was modulated mostly by effects on electrophilicity of the boronic acid group, one might expect electron withdrawing groups at the 2 and 4 positions to be about equal activators, but both to be better than similar groups at the 3 position. Instead, it was found that derivatives at the 3 position were more active than ones at 4, and that groups at 2 are much less active than either derivatives at 3 or 4. This is consistent with the steric constraints around the 2 position of MAPB and the polar environment around position 3 in the "MAPB-like" orientation. It was also found that the (S) and (R) stereoisomers of 3-tetrahydrofuranyl boronic acid differ in affinity for AmpC by an order of magnitude. This can only be explained by differential non-covalent interactions with the enzyme, perhaps with the nearby Thr316 residue if these ligands assume a "MAPB-like" binding mode.

Perturbations that maintained the overall steric disposition of MAPB, but changed its functionality, were next considered. In the case of a "MAPB-like" binding mode,

TABLE 1

| Inhibitor complex | Resolution range | Data Completeness | R-merge | R-factor R-free (%) | Space Group, cell dimensions (Å; deg.) |
|---|---|---|---|---|---|
| BZBTH2B | 20–2.25 | 87% | 9.4 | 17.9, 22.4 | C2; a = 119, b = 78, c = 99 $\alpha = \gamma = 90; \beta = 116$ |
| 3NPB | 20–2.15 | 95% | 8.4 | 22, 25 | C2; a = 121, b = 78, c = 100 $\alpha = \gamma = 90; \beta = 117$ |
| MAPB | 20–2.3 | 95% | 8.8 | 19.5, unknown | C2; a = 119, b = 77, c = 98 $\alpha = \gamma = 90.0; \beta = 116$ |

Structural modeling was followed by testing for inhibition of enzyme activity and antibacterial activity. This was followed by modeling and testing of additional compounds. For testing results, see Examples 2–5. This cycle of structural modeling, enzymatic testing and antibacterial evaluation led to the following observations.

An intriguing feature of the MAPB—AmpC complex is how few obviously favorable interactions are observed between the aryl group of the inhibitor and the enzyme. Still, MAPB has a $K_i$ of 7.3±0.9 $\mu$M for AmpC. One possible explanation for the affinity of MAPB is that the binding of the compound is driven by ligand hydrophobicity. To test this, the inhibition of several other hydrophobic boronic acids was measured. Both 1-naphthyl- and 9-phenanthreneboronic acids have two to three-fold worse (higher) dissociation constraints than MAPB. These ligands are larger than MAPB, so the effect of hydrophobicity may be complicated hydrogen-bonding groups from Asn289, Asn346, and Arg349 are in proximity to potential ring substituents at the 3- and 4-positions of a MAPB-like compound. Alternatively, if the boronic acid ligand binds in a "phosphonate-like" orientation, hydrogen-bonding groups from Gln120 and Asn152 lie nearby. It should be noted that, with the many approximations used in the boronic acid-based ligand modeling (no allowance for enzyme flexibility, simplistic modeling of ligand electrostatic properties, etc.), these results should only be used as a guide. In the case of either binding mode, it seemed reasonable to look for ligand functionality that could be involved in hydrogen bonds with, or at least offer polar complements to, these nearby residues. Consistent with these structural considerations, the $K_i$ values of the 3-nitro-, and 3-trifluoro derivatives of phenylboronic acid are in the one to two micromolar range, three- to five-fold better than MAPB. However, the 3-carboxy derivative of phenylboronic acid does not display significant affinity for AmpC ($K_i$>100 µM). This suggests that this compound cannot bind to AmpC in a manner that allows interaction between the m-substituent of the inhibitor and the Arg349 residue of the enzyme.

Three regions of the enzyme were of particular interest. Assuming a "MAPB-like" binding mode for boronic acid-based ligands, a "canyon" was noted near position 3 of the MAPB ring in the crystallographic complex. In addition, a large hydrophilic tunnel, about 15 Å in length, was noted near the 4-position of MAPB in the crystallographic complex that ran through the surface of the enzyme. Alternatively, if, as the modeling results suggest, a potential boronic acid ligand may also adopt a "phosphonate-like" binding orientation, the pocket defined by residues Ala318, Tyr221, Gln120, and Asn152 offers the potential for increasing ligand interactions with the target site by changing ligand functionality.

Surprisingly, the 4,4'-biphenyldiboronic acid analog inhibits AmpC potently, with a $K_i$ of 0.18±0.02 µM. Although this derivative may be modeled to fit near the mouth of the tunnel region of AmpC noted earlier, it cannot do so without accommodation on the part of the enzyme. If the same mode of binding as MAPB is assumed, without enzyme relaxation, this inhibitor would come into close contact with Ser287, Asp288, Asn289, and Asn346. Although modeling results suggest other conformations are possible, none of them make interactions that clearly explain the affinity of this compound. The most conservative explanation is that the 4,4'-biphenyldiboronic acid analog maintains the overall disposition of groups suggested by the MAPB-E. coli complex. This would lead to interactions with the mouth of the tunnel region, including residues such as Ala292. However, in order to do so, residues Asn346 and Ser287 would have to move slightly away from the ligand.

The proximity of the hydroxyl groups of Tyr150 and Thr316 to ring atoms of MAPB in the crystallogrphic complex suggested that polar or polarizable atoms at positions 2 or 3 might better complement the enzyme than the phenyl ring of MAPB. Consistent with this view, thiophene-2-boronic acid was found to have a $K_i$ of 2.5±0.4 µM against AmpC, and (R)-3-tetrahydrofuranyl-boronic acid was found to have a $K_i$ of 1.4±0.1 µM. The thiopene-3-boronic acid, which should be unable to accept a hydrogen bond from Tyr150 in a "MAPB-like" binding orientation, has a much worse affinity for AmpC ($K_i$=22.1±3.5 µM). The (S)-3-tetrahydrofuranylboronic acid, the heteroatom of which, in a "MAPB-like" binding orientation should be unable to interact with Thr316, has a $K_i$ of 15.8±0.8 µM. On the other hand, the poor affinity of 2-furanylboronic acid ($K_i$>>100 µM), which, like the 2-thiophene derivative, should be able to accept a hydrogen bond from Tyr150, is difficult to explain simply based on hydrogen bonding considerations. The differential activity of the 2-thiophene derivative relative to the 2-furanyl derivative might reflect subtle differences in polarity and polarizability of an aryl sulfur versus an aryl oxygen. Alternatively, the difference in activities might reflect the different shapes of the molecules.

It was also considered that substitutions, including the presence of larger heteroaryl groups, might improve the potency of TH2B. Modeling suggested that although ligands containing larger systems like benzo[b]heteroarylboronic acids probably would not fit into the AmpC site in a "MAPB-like" binding mode (based on orientation distributions and assuming no accommodation on the part of the enzyme), these compounds should still be able to bind to the enzyme in other productive orientations. Several derivatives of TH2B were tested, the most potent of which was benzo[b]thiophene-2-boronic acid. This compound has a $K_i$ of 27 nM for AmpC.

Benzo[b]thiophene-2-boronic acid is approximately 200-fold more active than thiophene-2-boronic acid, suggesting that interactions with the second aryl ring contribute considerably to affinity. This inference is supported by the activity of benzo[b]furan-2-boronic acid, which is about 1000-fold more active than the furan-2-boronic acid parent. At the same time, a comparison of the activity of BZBTH2B with 2-naphthylboronic acid ($K_i$=8.5±1.8 µM), which should place its distal aryl ring in approximately the same area as the benzo[b]thiophene derivative, confirms the importance of the thiophene ring. Model building suggests that BZBTH2B may bind to AmpC in the pocket defined by residues Gln120, Asn152, and Tyr218.

The wide variety of chemical functionality present in the boronic acid compounds tested has allowed mapping of the AmpC binding site and suggested modifications to improve the potency of the agents tested. Modeling of these inhibitors suggests that they may be interacting with the enzyme in ways unanticipated by earlier classes of inhibitors. At the same time, it must be admitted that such modeling carries with it some ambiguity and key questions regarding the structural bases for activity remain unanswered.

Example 2

Testing of Compounds for Inhibition of β-Lactamases

Compounds were tested for inhibition of TEM-1 and AmpC β-lactamases from *E. coli* using a spectrophotometric assay (Page, *Biochem. J*., 295, 295–304 (1993)). AmpC was prepared as described in Example 1. TEM-1 was provided by Natalie Strynadka, University Of Alberta, Edmonton, Canada. Alternatively, TEM-1 may be produced as follows. The TEM-1 gene is cloned into HpaI site of pALTER-EX2 (Promega). The gene is under control of the T7 promoter which is turned on for protein expression. TEM-1 may be expressed in JM109 cells, as well as several other *E. coli* strains. Cells are grown to late log phase, followed by induction of protein expression. The cells are spun down and the supernatant, into which the enzyme has been exported, is collected. Because the enzyme has been exported into the supernatant, purification may be achieved using standard column chromatography, as described in Matagne et al. *Biochem J*. 265, 131–146 (1990); Escobar et al, *Biochemistry* 33, 7619–7626 (1994).

Initial stock solutions of 1–100 mM concentrations of each compound to be tested were prepared in DMSO (dimethyl sulfoxide). Solubility and absorbance profiles were determined by incremental addition of small volumes of DMSO stock solutions to assay buffer (50 mM phosphate, pH 7.0) at 25° C. using an HP8543 UV/Visible spectrophotometer with multi-cell transport running HP ChemStation software (version 2.5). Enzymatic testing was typically started at an upper concentration limit determined by the solubility and absorbance profile of the compound.

Standard assay conditions for AmpC were as follows: pH 7.0; 100 µM cephalothin, sodium salt, as substrate; reaction monitored at 265 nm (cephalothin β-lactam absorbance peak); T=25° C.; 50 mM phosphate buffer; no incubation of inhibitor with enzyme; cycle times of 10–15 seconds; total reaction volume=1 mL; run time=5 minutes; reaction initialized with addition of 0.06 nM AmpC. The background rate of cephalothin hydrolysis under these conditions was found to be two to three orders of magnitude less than the rate of the enzyme-mediated cephalothin hydrolysis, so no correction for background hydrolysis of substrate was used. For TEM-1, 100 μM 6-β-furylacryloylamidopenicillanic acid, triethylammonium salt (FAP), was used as the substrate, the reaction was monitored at 340 nm (FAP β-lactam absorbance peak) and the cycle time was increased to 25 seconds (since this substrate was somewhat light sensitive). Due to the light sensitivity of FAP, the background rate of hydrolysis for this substrate was found to be minimal, but not insignificant, so all measured control and inhibited cell rates were corrected by subtraction of the FAP background rate. All other conditions for the TEM-1 assays were identical to those for the AmpC assays. DMSO was added to enzyme controls in all cases. Standard 1 mm path length quartz spectrophotometric cells (Hellma Cells, Inc., Jamaica, N.Y.) were used in the assays. All assays were performed on the same HP8543 spectrophotometer noted earlier.

Linear and quadratic fits to the absorbance data for the full time course of each reaction were used to determine the reaction rate for each spectrophotometric cell. The resulting reaction rate data were used to calculate the inhibition constants for each potential inhibitor using the method of Waley (S. G. Waley, *Biochem. J.* 205, 631–633 (1982)). Briefly, this method involves the use of the integrated Michaelis-Menten equation to calculate $K_i$ values for enzyme inhibitors from a comparison of the reaction rates of uninhibited and inhibited enzymatic reactions.

Specificity testing was performed by assaying the activity of an inhibitor against α-chymotrypsin (bovine pancreatic), β-trypsin (bovine pancreatic), and elastase (porcine pancreatic). Substrates for α-chymotrypsin (N-benzoyl-L-tyrosine ethyl ester, BTEE) and β-trypsin (N-benzoyl-L-arginine ethyl ester, BAEE) were purchased from Sigma Chemical, St. Louis, Mo. The elastase substrate used (elastase substrate 1, Nα-methoxysuccinyl-Ala-Ala-Pro-Val-p-nitroanilide, was purchased from Calbiochem, San Diego, Calif. All enzymes used for specificity testing were purchased from Sigma Chemical, St. Louis, Mo. For α-chymotrypsin, 3 μl of a 1 mg/ml enzyme stock solution (50 mM phosphate buffer, pH 7) was incubated with the boronate being tested for 5 minutes; then the reaction was initialized by addition of 630 μM BTEE from a DMSO stock solution. The reaction was performed at 25° C. and monitored at 260 nm. For β-trypsin, 40 μl of a 0.8 mg/ml enzyme stock solution (50 mM phosphate buffer, pH 7) was incubated with the boronate being tested for 5 minutes; then the reaction was initialized by addition of 600 μM BAEE from a DMSO stock solution. For elastase, 50 μl of a 1 mg/ml enzyme stock solution (50 mM phosphate buffer, pH 7) was incubated with the boronate being tested for 5 minutes; then the reaction was initialized by addition of 64 μM elastase substrate 1 from a DMSO stock solution.

The compounds tested are those listed in Tables 2A and 2B below. Certain prior art compounds (marked with an * in Table 2A) were tested for comparative purposes. 9-Phenanthreneboronic acid (9PHNB) was obtained from TCI America, Portland, Oreg. Butylboronic acid (BUTB), 4-bromophenylboronic acid (4BPB), 3-nitrophenylboronic acid (3NPB), 2-hydroxy-5-(3-(trifluoromethyl)phenylazo) benzeneboronic acid (HFAB), 2,4,6-tris(5-(4-bromophenylazo)-2-hydroxyphenyl) boroxin (4BPAPB), and diethanolamine-(3R)-(+)-tetrahydrofurnylboronate (DETHFB) were obtained from Aldrich Chemical, Milwaukee, Wis. (HFAB and 4BPAPB are products of the Sigma-Aldrich Library of Rare Chemicals). The remaining compounds tested were obtained from Lancaster Synthesis, Windham, N.H. All compounds were used as is with no additional purification or verification performed.

Figure 1E:
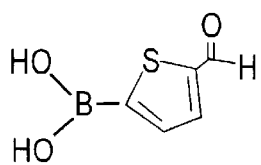
Figure 1E:
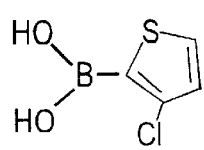
Figure 1E:
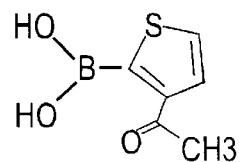
Figure 1E:
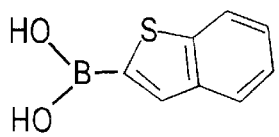
Figure 1E:
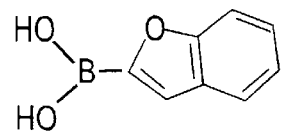

The results of the testing are presented in Tables 2A, 2B and 2C below. Tables 2A and 2B contain the results of the assays of inhibition of AmpC and TEM-β-lactamases, and Table 2C contains the results of the specificity testing. In the tables, N.T.=not tested, and N.A.=not active at the maximum inhibitor concentration tested. Other abbreviations used in Tables 2A, 2B and 2C which are not explained in this example are explained in FIGS. 1A, 1D and 1E.

TABLE 2A

| boronate | Ki *E. coli* AmpC (μM) | Ki *E. coli* TEM-1 (μM) |
|---|---|---|
| borinic acids | | |
| DFB | >500 | >>100 |
| acyclic alkylboronates | | |
| BUTB | >500 | >100 |
| heterocyclic alkylboronates | | |
| RDETHFB | 1.1 | 27.0 |
| SDETHFB | 15.0 | 86.2 |
| arylboronates | | |
| BIPD | 0.6 | >>100 |
| HFAB | 1.3 | N.T. |
| 3TFMB | 1.6 | 85.0 |
| NSULFB* | 1.6 | 88.0 |
| 3NPB | 1.9 | 24.0 |
| 4BPB | 2.6 | 31.3 |
| 4FORMB* | 2.8 | 35.0 |
| 4MEPB* | 5.2 | >100 |
| MAPB* | 5.8 | >>100 |
| 4COOHB | 5.8 | >>100 |
| 4FB | 6.1 | >>100 |
| B14DA | 6.9 | 40.0 |
| 4BPAPB | 7.2 | 1.2 |
| 4MEOB | 7.7 | >100 |
| 2FDB* | 8.0 | >100 |
| 4TFMB | 9.0 | 6.3 |
| NAPB | 10.4 | 34.0 |
| 9PHNB | 12.6 | 31.0 |
| 2FORMB* | 62.0 | >100 |
| heterocyclic arylboronates | | |
| TH2B | 3.3 | 31.0 |
| TH3B | 17.0 | 100.0 |

TABLE 2B

| boronate | Ki *E. coli* AmpC (μM) | Ki *E. coli* TEM-1 (μM) |
|---|---|---|
| BZBTH2B | 0.04 | 4.0 |
| BZBF2B | 0.07 | 8.0 |

TABLE 2B-continued

| boronate | Ki E. coli AmpC (µM) | Ki E. coli TEM-1 (µM) |
|---|---|---|
| 5CLTH2B | 1.4 | 17.0 |
| 5ACTH2B | 1.8 | >50 |
| TH2B | 3.3 | 31.0 |
| 3FTH2B | 3.5 | N.I. |

N.I. = no inhibition observed at an inhibitor concentration of 100 µM.

TABLE 2C

| boronate | IC50 (µM) for: | | | |
|---|---|---|---|---|
| | AmpC | CHT | TRY | ELST |
| TH2B | 10.0 | >200.0 | >200.0 | 100.0 |

CHT = alpha-chymotrypsin, bovine pancreas;
TRY = beta-trypsin, bovine pancreas;
ELST = elastase, porcine pancreas Example 3

Antibacterial Activity

Bacterial cell culture testing was performed and interpreted following the guidelines of the National Committee for Clinical Laboratory Standards (National Committee for Clinical Laboratory Standards. Methods for Dilution Antimicrobial Susceptibility Tests for Bacteria that Grow Aerobically. Approved Standard M7-A3. National Committee for Clinical Laboratory Standards, Villanova, Pa. 1993). After incubation, the growth of the cells was visually inspected. The minimum inhibitory concentration (MIC) is the lowest concentration where there no cell growth was observed. The results are presented in the tables below.

The following strains were used: Enterobacter cloacae cell line with derepressed β-lactamase production (Ent-Der), and Escherichia coli RYC1000 (araD139 D lacU169 rpsL D rib7 thiA gyrA recA56) cell lines, harboring the plasmid pBGS19 (with no β-lactamase), or the β-lactamase containing plasmids pBGAmpC (AmpC β-lactamase from E. coli; Eco-AmpC), or pBGAmpC-MHN (AmpC β-lactamase from Enterobacter cloacae; Eco-AmpCEnt). Plasmids pBGAmp-MHN and pBGAmpC were constructed by PCR amplification of the respective E. cloacae and E. coli chromosomal ampC genes and subsequent cloning into pBGS18 (Spratt, B. G.; Hedge, P. I.; Heesen, S.; Edelman, A.; Broome-Smith, J. K. Gene 41, 337–342 (1986)). TEM-10 and TEM-24 are mutants of TEM-1. TEM-10 and TEM-24 differ from TEM-1 due to the following point substitutions: TEM-10 (R164S, E240K); TEM-24 (L102K, L162S, S235T, A237K). TEM-10 and TEM-24 also differ from TEM-1 in being extended spectrum enzymes (i.e., they react with a greater range of substrates than TEM-1). Also tested were clinical isolates of Pseudomonas aeruginosa. All bacterial strains and plasmids are available from Jesus Blazquez and Fernando Baquero, Servicio de Microbiologia, Hospital Ramon y Cajal, National Institute of Health, Madrid, Spain.

Boronic acid inhibitors were tested over a range of concentrations up to a maximum of 128 µg/ml. Several ratios, including 1:1, 2:1, 4:1, and 1:3, of β-lactam antibiotic (amoxicillin (AX) or ceftazidime (CAZ)) to boronic acid compound were used in the assays. Tazobactam (TAZO), a clinically used β-lactamase inibitor, was used as a positive control.

TABLE 3A

Activity of boronic acid derivatives against bacterial cells in combination with ceftazidime.
MICs of ceftazidime (CAZ) and ceftazidime plus inhibitor (proportion: 4/1) in pg/ml. Strains used were: E. coli RYC1000 (which does not produce β-lactamase) harboring plasmid pBGS19 (which produces no β-lactamase), same strain harboring plasmid pBGTEM-24 (coding for TEM-24 β-lactamase, a mutant of TEN-1) or plasmid PBGAmpC-MHN (coding for AmpC β-lactamase of Enterobacter cloacae), and a β-lactamase derepressed strain of Enterobacter cloacae (Ent. Der.). "Tazo" is tazobactam, a clinically used β-lactam-based β-lactamase inhibitor (Lederle Laboratories, Pearl River, NY).

| | CAZ | BIPD | 9PHNB | DETHFB | 3NBP | TH2B | 48PAPB | BZBTH2B | 5CLTH2B | TAZO |
|---|---|---|---|---|---|---|---|---|---|---|
| pBGS19 | <0.5 | <0.12 | <0.25 | 0.5 | <0.25 | <0.25 | <0.25 | <0.25 | <0.25 | <0.25 |
| TEM-24 | 256 | 256/64 | 256/64 | 256/64 | 126/32 | 126/32 | 256/64 | 128/32 | 128/32 | 8/2 |
| AmpC-MHN | 32 | 8/2 | 8/2 | 4/1 | 4/1 | 8/2 | 8/2 | 2/0.5 | 4/1 | 4/1 |
| Ent. Der. | 512 | 128/32 | 512/128 | 32/8 | 32/8 | 32/8 | 512/128 | 32/8 | 32/8 | 32/8 |

TABLE 3B

Activity of boronic acid derivatives against
bacterial cells when used by themselves.
MICs of inhibitors when used alone without ceftazidime,
in pg/ml. The strains and plasmids are the same as for Table 3A.

|  | BIPD | 9PHNB | DETHFB | 3NPB | TH2B | 4BPAPB | BZBTH2B | 5CLTH2B |
|---|---|---|---|---|---|---|---|---|
| PBGS19 | >256 | 128 | >512 | 64 | 128 | 128 | 512 | 128 |
| TEM-24 | >256 | 128 | >512 | 128 | 128 | 256 | 512 | 128 |
| AmpC-MHN | >256 | 256 | >512 | 256 | 128 | 256 | 512 | 128 |
| Ent. Der. | >256 | >512 | >512 | >512 | 256 | >512 | 512 | 128 |

TABLE 4A

Activity of boronic acid derivatives against bacterial cells in combination with amoxicillin.
MICs of amoxicillin (AX) and amoxicillin plus inhibitor (proportion: 4/1) in ug/ml.
Strains used were: E. coli RYC1000 harboring plasmid pBGS19 producing no β-lactamase
(EC), the same harboring pBGTEM-1 producing TEM-1 β-lactainase (EC-T1), harboring
pBGTEM-10 producing TEM-10 β-lactamase, a mutant of TEM-1 (EC-T10), harboring
pBGAmpC-MHN (EC-AmpCEn), harboring pBGAmpC-E. coli producing AmpC (ECR-AmpCEc), harboring a plasmid coding for a mutant of AmpC from Enterobacter
(ECR-AmpCEnM), and a β-lactamase derepressed strain of Enterobacter cloacae (Ent-Der).

|  | AX | BIPD | DETHFB | 9PHNB | 3NPB | TH2B | TAZO |
|---|---|---|---|---|---|---|---|
| EC |  |  |  |  |  |  |  |
| EC-T1 | >2,048 | 256 | 512 | 512 | 256 | 128 | 8 |
| EC-T10 | >2,048 | 256 | 512 | 512 | 256 | 256 | 4 |
| EC-AmpCEn | >2,048 | 128 | 32 | 256 | 64 | 32 | 16 |
| ECR-AmpCEc | >2,048 | 128 | 128 | 512 | 64 | 64 | 32 |
| ECR-AmpCEnM | >2,048 | 128 | 64 | 64 | 32 | 32 | 16 |
| Ent-Der. | >2,048 | 256 | 256 | 512 | 256 | 64 | 128 |

TABLE 4B

Activity of boronic acid derivatives against
bacterial cells when used by themselves.
MICs of inhibitors when used alone without amoxicillin,
in μg/ml. The strains and plamids are the same as for Table
4A. The compounds were not tested above 128 μg/ml; here,
"256" indicates no inhibition of cell growth.

|  | BIPD | DETHFB | 9PHNB | 3NPB | TH2B | TAZO |
|---|---|---|---|---|---|---|
| EC | 256 | 256 | 256 | 256 | 64 | 32 |
| EC-T1 | 256 | 256 | 256 | 64 | 64 | 32 |
| EC-T10 | 256 | 256 | 256 | 128 | 128 | 64 |
| EC-AmpCEn | 256 | 256 | 256 | 256 | 128 | 64 |
| ECR-AmpCEc | 128 | 256 | 256 | 128 | 128 | 64 |
| ECR-AmpCEnM | 256 | 256 | 256 | 128 | 64 | 64 |
| Ent-Der. | 256 | 256 | 256 | 128 | 128 | 256 |

TABLE 4C

Activity of TH2B against Pseudomonas aeruginosa in
combination with ceftazidime.

| Inhibitor | Organism | β-lactamase Expressed | MIC cell culture CAZ alone (μg/ml)[a] | MIC cell culture CAZ/TH2B (μg/ml)[a] |
|---|---|---|---|---|
| TH2B | Pseudomanas aeruginosa | AmpC (clinical isolates) | 128 | 8/10* |

TABLE 4C-continued

Activity of TH2B against Pseudomonas aeruginosa in
combination with ceftazidime.

| Inhibitor | Organism | β-lactamase Expressed | MIC cell culture CAZ alone (μg/ml)[a] | MIC cell culture CAZ/TH2B (μg/ml)[a] |
|---|---|---|---|---|

[a]Broth dilution assays against the Pseudomonas aeruginosa clinical isolates (from Hospital Ramon y Cajal in Madrid, Spain). The inhibitors were used in combination with ceftazidime (CAZ). The concentration of CAZ was varied by serial dilution, at a constant concentration of TH2B of 10 μg/ml. Dilution average of 11 clinical isolates. Range was 1/10 CAZ/TH2B to 64/10 CAZ/TH2B.

Example 4

Testing of Compounds for Inhibition of β-Lactamases

Additional compounds were tested for inhibition of AmpC β-lactamase as described in Example 2. The results are presented in Table 5 below. The last two compounds in Table 5 were synthesized by Key Organics, Cornwall, UK. The other compounds in Table 5 were obtained from Lancaster Synthesis, Windham, N.H., Aldrich Chemical, Milwaukee, Wis., or Frontier Scientific, Logan, Utah.

TABLE 5

$$\text{HO-B(OH)-R}$$

| R | Ki AmpC (μM) |
|---|---|
| 6-methyl-naphthalen-2-yl | 8.5 ± 1.8 |
| 6-methyl-1,3-benzodioxol-5-yl | 53.4 ± 6.1 |
| 5-methyl-1H-indol-6-yl | 10.9 ± 0.6 |
| 3-methyl-5-carboxyphenyl | >>100 |
| (E)-3-(3-methylphenyl)ethenyl-COOH | 5.9 ± 0.3 |
| (E)-3-(4-methylphenyl)ethenyl-COOH | 4.2 ± 1.1 |
| (R)-tetrahydrofuran-3-yl | 1.4 ± 0.1 |
| (S)-tetrahydrofuran-3-yl | 15.8 ± 0.8 |
| 5-methyl-furan-2-yl | >>100 |
| 2-methyl-4-methyl-thiophen-5-yl | 0.50 ± 0.05 |

TABLE 5-continued $$\text{HO-B(OH)-R}$$

| R | Ki AmpC (μM) |
|---|---|
| 3-methyl-benzo[b]thiophen-2-yl | 0.78 ± 0.08 |
| 4-(2-(3-methylphenyl)hydrazono)-isochroman-1,3-dione | 0.075 |
| 2-methyl-4-(2-(3-methylphenyl)hydrazono)-isoquinoline-1,3(2H,4H)-dione | 0.075 |

Example 5

Antibacterial Activity

Two compounds (BZB and TH2B) were tested as described in Example 3 against a wider range of bacteria using CAZ as the β-lactam antibiotic. All bacterial strains and plasmids are available from Jesus Blazquez and Fernando Baquero, Servicio de Microbiologia, Hospital Ramon y Cajal, National Institute of Health, Madrid, Spain. The results are presented in Table 6 below.

TABLE 6

| Species/Enzyme Expressed | CAZ alone | BZB only | CAZ-BZB | CAZ-TH2B |
|---|---|---|---|---|
| MC4100/AmpC-Enter | 32 | | 1 | 4 |
| MC4100/AmpC-*E. coli* | 8 | | 1 | 2 |
| MC4100/AmpC-Enter (OmpR−) | 32 | | 1 | 4 |
| MC4100/AmpC-*E. coli* (OmpR−) | 8 | | 2 | 2 |
| MC4100/AmpC-Enter (OmpC−) | 16 | | 1 | 2 |
| MC4100/AmpC-*E. coli* (OmpC−) | 16 | | 1 | 2 |
| MC4100/AmpC-Enter (OmpF−) | 32 | | 1 | 4 |
| MC4100/AmpC-*E. coli* (OmpF−) | 32 | | 1 | 2 |
| *Pseudomonas aeruginosa*-1 (clinical isolate) | 8 | 512 | 8 | |
| *Ps. aeruginosa*-2 (clinical isolate) | 32 | 512 | 4 | |
| *Ps. aeruginosa*-3 (clinical isolate) | 64 | 512 | 4 | |
| *Enterobacter cloacae* derrepressed (clinical isolate) | 16 | 128 | 2 | |

TABLE 6-continued

| Species/Enzyme Expressed | CAZ alone | BZB only | CAZ-BZB | CAZ-TH2B |
|---|---|---|---|---|
| *E. coli* derrepr. (clinical isolate) | 16 | 128 | 2 | |
| *Citrobacter freundii* derrepressed (clinical isolate) | 16 | 128 | 2 | |

MC4100 is a strain of *E. coli* available from the American Type Culture Collection, Rockyille, MD, accession number 35695.
For AmpC plasmids, see Example 3.
OmpC and OmpF are porin channel proteins associated with the expression of porin channels.
OmpR is a regulatory protein that governs the expression of OmpF and OmpC.
"–" indicates a mutant lacking one of these proteins that the wild-type bacteria would ordinarily have.
The clinical isolates are from Hospital Ramon y Cajal in Madrid, Spain.

We claim:

1. A method of treating a β-lactam-antibiotic-resistant bacterial infection comprising administering to an animal suffering from such an infection an effective amount of a compound which is a β-lactamase inhibitor, the compound having the formula:

(1) $(OH)_2—B—R$ wherein:

R is naphthalene, phenanthrene, or has one of the following formulas:

(2)
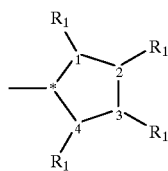

(4)
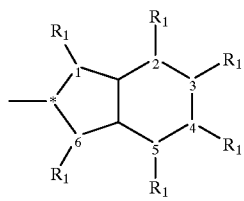

(5)
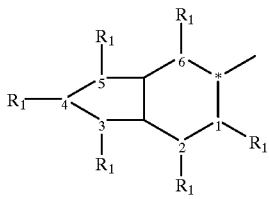

(6)
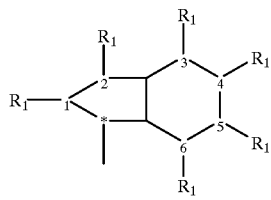

(7)
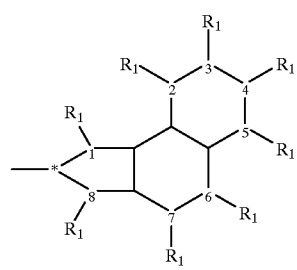

(8)
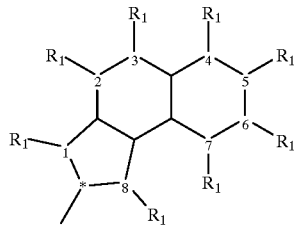

(9)
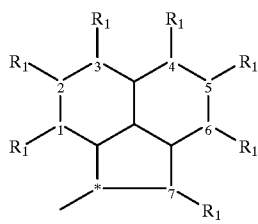

(10)
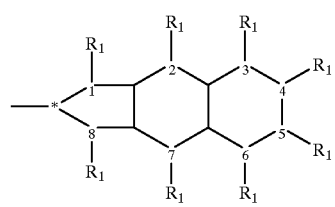

(13)
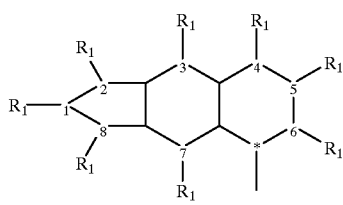

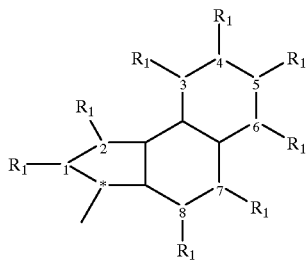
(14)

wherein
ring system (2), (4), (5), (6), (7), (8), (9), (10), (13) or (14) is aromatic or nonaromatic;
the atom center * is (R) or (S) in the case of chiral compounds;
positions 1, 2, 3, 4, 5, 6, 7 or 8 each independently is C, O or S;
each $R_1$ independently is a lone pair, H, $B(OH)_2$, a halogen atom, $CF_3$, $CH_2CF_3$, $CCl_3$, $CH_2CCl_3$, $CBr_3$, $CH_2CBr_3$, $NO_2$, lower alkyl, $CO_2H$, CHCHCOOH, $CH_2CH_2CH_2COOOH$, $SO_3H$, $PO_3H$, $OSO_3H$, $OPO_3H$, OH, $NH_2$, $CONH_2$, $COCH_3$, $OCH_3$, or phenyl boronic acid;
or a pharmaceutically-acceptable salt thereof; and
an effective amount of a β-lactam antibiotic.

2. The method of claim 1 wherein R is (4).
3. The method of claim 2 wherein atom 1 is S or O and the remaining atoms 2–6 are carbons.
4. The method of claim 3 wherein the compound is benzo[b]furan-2-boronic acid or benzo[b]thiophene-2-boronic acid.
5. The method of claim 1 wherein R is (6).
6. The method of claim 5 wherein the compound is benzo[b]thiophene-3-boronic acid.
7. The method of claim 1 wherein R is (2).
8. The method of claim 7 wherein atom 1 is S and the remaining atoms 2–4 are carbons or atom 2 is S or O and the remaining atoms 1 and 3–4 are carbons.
9. The method of claim 8 wherein the compound is thiophene-2-boronic acid, 3-formylthiophene-2-boronic acid, 5-chlorothiophene-2-boronic acid, 4-methythiophene-2-boronic acid, 5-acetylthiophene-2-boronic acid, or R-3-tetrahydrofuranylboronic acid.
10. The method of claim 1 wherein the β-lactam antibiotic is amoxicillin or ceftazidime.
11. A method of inhibiting a β-lactamase comprising contacting the β-lactamase with an effective amount of a compound having the formula:

$(OH)_2$—B—R     (1)

wherein:

R is naphthalene, phenanthrene, or has one of the following formulas:

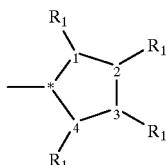
(2)

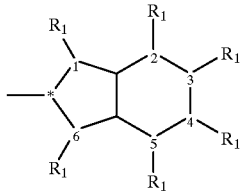
(4)

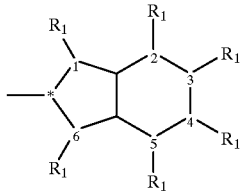
(5)

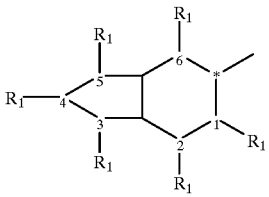
(6)

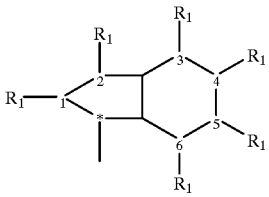
(7)

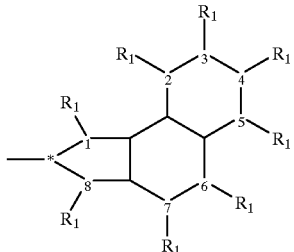
(8)

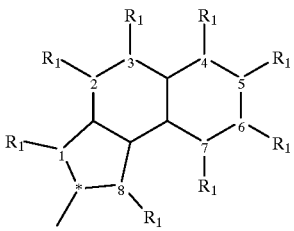
(9)

(10)

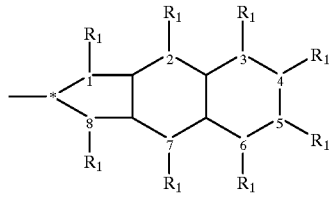

(13)

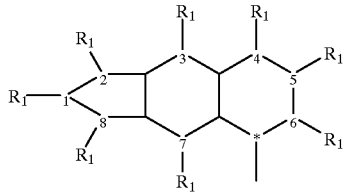

(14)

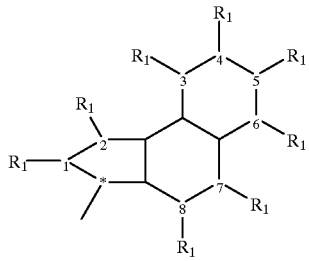

wherein:

ring system (2), (4), (5), (6), (7), (8), (9), (10), (13) or (14) is aromatic or nonaromatic;

the atom center * is (R) or (S) in the case of chiral compounds;

positions 1, 2, 3, 4, 5, 6, 7 or 8 each independently is C, N, O or S;

each $R_1$ independently is a lone pair, H, $B(OH)_2$, a halogen atom, $CF_3$, $CH_2CF_3$, $CCl_3$, $CH_2CCl_3$, $CBr_3$, $CH_2CBr_3$, $NO_2$, lower alkyl, $CO_2H$, CHCHCOOH, $CH_2CH_2C_2CH_2COOH$, $SO_3H$, $PO_3H$, $OSO_3H$, $OPO_3H$, OH, $NH_2$, $CONH_2$, $COCH_3$, $OCH_3$, or phenyl boronic acid;

or pharmaceutically acceptable salts thereof.

12. The method of claim 11 wherein the β-lactamase is produced by bacteria, and the bacteria are contacted with the compound or salt thereof.

13. The method of claim 11 wherein the contacting takes place in vitro.

14. A pharmaceutical composition comprising a compound which is a β-lactamase inhibitor having the formula:

(1)

wherein:

R is naphthalene, phenanthrene, or has one of the following formulas:

(2)

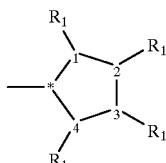

(4)

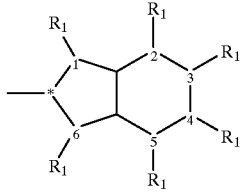

(5)

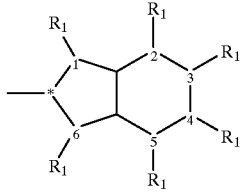

(6)

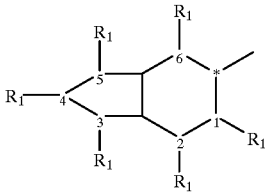

(7)

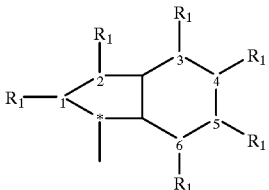

(8)

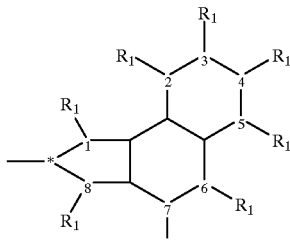

(9)

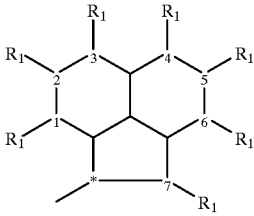

-continued

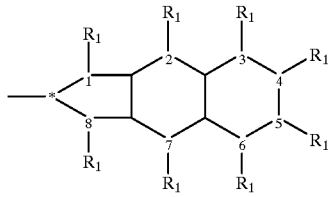
(10)

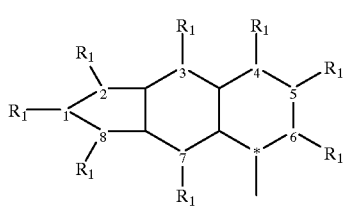
(13)

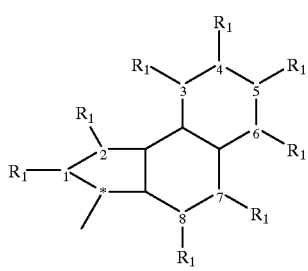
(14)

wherein:
ring system (2), (3), (4), (5), (6), (7), (8), (9), (10), (13) or (14) is aromatic or nonaromatic;
the atom center * is (R) or (S) in the case of chiral compounds;
positions 1, 2, 3, 4, 5, 6, 7 or 8 each independently is C, O or S;
each $R_1$ independently is a lone pair, H, $B(OH)_2$, a halogen atom, $CF_3$, $CH_2CF_3$, $CCl_3$, $CH_2CCl_3$, $CBr_3$, $CH_2CBr_3$, $NO_2$, lower alkyl, $CO_2H$, CHCHCOOH, $CH_2CH_2CH_2COOH$, $SO_3H$, $PO_3H$, $OSO_3H$, $OPO_3H$, OH, $NH_2$, $CONH_2$, $COCH_3$, $OCH_3$, or phenyl boronic acid;
or pharrnaceutically-acceptable salts thereof.

15. The composition of claim 14 wherein R is (4).

16. The composition of claim 15 wherein atom 1 is S or O and the remaining atoms 2–6 are carbons.

17. The composition of claim 16 wherein the compound is benzo[b]furan-2-boronic acid or benzo[b]thiophene-2-boronic acid.

18. The composition of claim 14 wherein R is (6).

19. The composition of claim 18 wherein the compound is or benzo[b]thiophene-3-boronic acid.

20. The composition of claim 14 wherein R is (2).

21. The composition of claim 20 wherein atom 1 is S and the remaining atoms 2–4 are carbons or atom 2 is S or O and the remaining atoms 1 and 3–4 are carbons.

22. The composition of claim 21 wherein the compound is thiophene-2-boronic acid, 3-formylthiophene-2-boronic acid, 5-chlorothiophene-2-boronic acid, 4-methylthiophene-2-boronic acid, 5-acetylthiophene-2-boronic acid, or R-3-tetrahydrofuranylboronic acid.

23. The composition of claim 14 further comprising a β-lactam antibiotic.

24. The composition of claim 23 wherein the β-lactam antibiotic is amoxicillin or ceftazidime.

* * * * *